US008894592B2

(12) United States Patent
Amundson et al.

(10) Patent No.: US 8,894,592 B2
(45) Date of Patent: Nov. 25, 2014

(54) DEVICE AND METHOD FOR DECREASING OXYGEN CONSUMPTION OF A PERSON DURING STEADY WALKING BY USE OF A LOAD-CARRYING EXOSKELETON

(75) Inventors: Kurt Amundson, Berkeley, CA (US); Russdon Angold, American Canyon, CA (US); Nathan Harding, Oakland, CA (US); Homayoon Kazerooni, Berkeley, CA (US)

(73) Assignees: University of California at Berkekey, Berkeley, CA (US); Ekso Bionics, Inc., Richmond, VA (US)

( * ) Notice: Subject to any disclaimer, the term of this patent is extended or adjusted under 35 U.S.C. 154(b) by 1179 days.

(21) Appl. No.: 12/468,487

(22) Filed: May 19, 2009

(65) Prior Publication Data
US 2010/0094185 A1   Apr. 15, 2010

Related U.S. Application Data

(60) Provisional application No. 61/071,824, filed on May 20, 2008.

(51) Int. Cl.
*A61H 3/00* (2006.01)
*B25J 9/00* (2006.01)
*A61F 5/01* (2006.01)

(52) U.S. Cl.
CPC .............. *B25J 9/0006* (2013.01); *A61H 3/008* (2013.01); *A61F 5/0102* (2013.01)
USPC ........ 601/35; 601/5; 601/23; 601/33; 602/16; 602/23; 128/898

(58) Field of Classification Search
CPC ........... A61H 3/00; A61H 3/008; A61H 1/00; A61H 1/02; A61H 1/0237; A61H 1/024; A61H 1/0244; A61H 1/0262; A61H 2001/00; A61H 2001/02; A61H 2001/0244; A61H 2001/0237; A61H 2003/00; A61H 2201/164; A61H 2201/1642; A61H 2201/1628; A61H 2201/163; A61H 2201/1676; A61F 5/01; A61F 5/0102

USPC ........ 601/5, 23, 24, 33, 34, 35; 602/5, 16, 23; 128/898
See application file for complete search history.

(56) References Cited

U.S. PATENT DOCUMENTS

| 406,328 A | 7/1889 | Yagn |
| 420,178 A | 1/1890 | Yagn |

(Continued)

FOREIGN PATENT DOCUMENTS

| JP | 2004188531 | 7/2004 |
| WO | WO 2006/113520 | 10/2006 |

OTHER PUBLICATIONS

Takaishi et al., Relationsip between muscle fatigue and oxygen uptake, European Journal of Applied Physiology (1992) 65:335-339.*

(Continued)

*Primary Examiner* — Quang D Thanh
(74) *Attorney, Agent, or Firm* — Diederiks & Whitelaw, PLC

(57) ABSTRACT

A lower extremity exoskeleton includes: at least one power unit; two leg supports designed to rest on the ground; two knee joints configured to allow flexion and extension between respective shank and thigh links of the leg supports; an exoskeleton trunk rotatably connectable to the leg supports; and two hip actuators configured to create torques between the exoskeleton trunk and the leg supports. In use, the hip actuators create a torque to move the leg supports backward relative to the exoskeleton trunk during a stance phase, which pushes the exoskeleton trunk forward. A second torque may be used to move the leg supports forward relative to the exoskeleton trunk into a swing phase. Additionally, a swing torque may be generated during the swing phase to move the leg support forward relative to the exoskeleton trunk. This results in decreased oxygen consumption and heart rate of a user wearing the exoskeleton.

23 Claims, 35 Drawing Sheets

(56) References Cited

U.S. PATENT DOCUMENTS

| | | | |
|---|---|---|---|
| 420,179 | A | 1/1890 | Yagn |
| 438,830 | A | 10/1890 | Yagn |
| 440,684 | A | 11/1890 | Yagn |
| 539,872 | A | 5/1895 | Kheiralla |
| 807,908 | A | 12/1905 | Bradstreet |
| 979,243 | A | 12/1910 | Anderson |
| 1,308,675 | A | 7/1919 | Kellley |
| 2,010,482 | A | 8/1935 | Cobb |
| 2,305,291 | A | 12/1942 | Filippi |
| 2,573,866 | A | 11/1951 | Murphy |
| 4,422,453 | A | 12/1983 | Salort |
| 4,557,257 | A | 12/1985 | Fernandez |
| 4,946,156 | A | 8/1990 | Hart |
| 5,016,869 | A | 5/1991 | Dick |
| 5,476,441 | A | 12/1995 | Durfee et al. |
| 6,171,272 | B1 | 1/2001 | Akita |
| 6,422,329 | B1 | 7/2002 | Kazerooni |
| 7,190,141 | B1 | 3/2007 | Ashrafiuon |
| 2002/0094919 | A1* | 7/2002 | Rennex et al. ............... 482/124 |
| 2003/0093021 | A1 | 5/2003 | Goffer |
| 2004/0158175 | A1 | 8/2004 | Ikeuchi |
| 2006/0052732 | A1 | 3/2006 | Shimada |
| 2006/0142105 | A1 | 6/2006 | Kudoh |
| 2006/0211956 | A1 | 9/2006 | Sankai |
| 2006/0249315 | A1 | 11/2006 | Herr |
| 2006/0258967 | A1 | 11/2006 | Fujil |
| 2006/0260620 | A1 | 11/2006 | Kazerooni |
| 2006/0276728 | A1* | 12/2006 | Ashihara et al. ............ 601/5 |
| 2007/0010378 | A1 | 1/2007 | Katoh |
| 2007/0016329 | A1 | 1/2007 | Herr |
| 2007/0027409 | A1 | 2/2007 | Katoh |
| 2007/0043449 | A1 | 2/2007 | Herr |
| 2007/0055189 | A1 | 3/2007 | Katoh |
| 2007/0056592 | A1 | 3/2007 | Angold |
| 2007/0078351 | A1* | 4/2007 | Fujita et al. ............... 600/500 |
| 2007/0106190 | A1 | 5/2007 | Katoh |
| 2007/0123997 | A1* | 5/2007 | Herr et al. ............... 623/27 |
| 2008/0009771 | A1 | 1/2008 | Perry |

OTHER PUBLICATIONS

Johnson, D., et al. "Development of a Mobility Assist for the Paralyzed, Amputee, and Spastic Patient." Proceedings of the Fifteenth Southern Biomedical Engineering Conference, IEEE, pp. 67-70, Dayton, Ohio, Mar. 1996.

Yamamoto, K., et al "Development of Power Assisting Suit for Assisting Nurse Labor." JSME International Journal Series C., vol. 45, No. 3, Sep. 2002.

Yamamoto, K., et al "Development of Power Assisting Suit (Miniaturization of Supply System to Realize Wearable Suit)." JSME International Journal Series C., vol. 46, No. 3, Sep. 2003.

Vukobratovic, M., et al. "Development of Active Anthropomorphic Exoskeletons." Medical and Biological Engineering, pp. 66-80, Jan. 1974.

Misuraca, J., et al, "Lower Limb Human Muscle Enhancer." Proceedings of the Symposium on Advances in Robot Dynamics and Control. ASME International Mechanical Engineering Congress and Exposition (IMECE), New York, New York, Nov. 2001.

Belforte, G., et al. "Pneumatic Active Gail Orthosis." Mechatronics, vol. 11, No. 3, pp. 301-323, Apr. 2001.

Kasaoka, K., et al "Predictive Control Estimating Operator's Intention for Stepping-up Motion by Exo-Sckeleton Type Power Assist System HAL," Proceedings of the IEEE/RSJ International Conference on Intelligent Robots and Systems (IROS), vol. 3, pp. 1578-1553, Maui, Hawaii, Nov. 2001.

Kawamoto, H., et al. "Comfortable Power Assist Control Method for Walking Aid by HAL-3." Proceedings of the IEEE International Conference on Systems, Man, and Cybernetics (SMC), vol. 4, Hammamet, Tunisia, Oct. 2002.

Lee, S. et al "Power Assist Control for Walking Aid with HAL-3 Based on EMG and Impedance Adjustment around Knee Joint" Proceedings of the IEEE/RSJ International Conference on Intelligent Robots and Systems (IROS), vol. 2, pp. 1499-1504, Lausanne, Switzerland, 2002.

Kawamoto, H., et al. "Power Assist System HAL-3 for Gait Disorder Person," Lecture Notes in Computer Science (LNCS), vol. 2398, Proceedings of the Eighth International Conference on Computers Helping People with Special Needs (ICCHP), pp. 196-203, Berlin, Germany, 2002.

Irby, S., et al. "Automatic Control Design for a Dynamic Knee-Brace System." IEEE Transactions on Rehabilitation Engineering. vol. 7, No. 2, pp. 135-139, Jun. 1999.

Ferris, D., et al "An Ankle-foot Orthosis Powered by Artificial Muscles," Proceedings of the 25th Annual Meeting of the American Society of Biomechanics, San Diego, California, Aug. 2001.

Naruse, K., et al "Design of Compact and Lightweight Wearable Power Assist Device." Proceedings of ASME International Mechanical Engineering Congress and Exposition (IMECE), Washington D.C., Nov. 2003.

Harley, J. A. "Design and Construction of an Underactuated Assistive Walking Device." Graduate Thesis, UC-Berkeley Mechanical Engineering Dept., Aug. 1995.

Zin Min Lim, Michael. "An Analysis on the Performance of an Underactuated Lower Extremity Enhancer," Graduate Thesis, UC-Berkeley Mechanical Engineering Dept., 2000.

Clark, D. C., et al. "Exploratory Investigation of the Man Amplifier Concept." Technical Documentary Report No. AMRL-TDR-62-89, United States Air Force, Wright-Patterson Air Force Base, Ohio, Aug. 1962.

"Machine Augmentation of Human Strength and Endurance : Hardiman I Prototype Project.", Report for ONR Contract N00014-66-C0051, Prepared by General Electric Company, Schenectady, New York, Jul. 1969.

"Research and Development Prototype for Machine Augmentation of Human Strength and Endurance : Hardiman I Project.", Report for ONR Contract Number. Report for ONR Contract N00014-66-C0051, Prepared by General Electric Company, Schenectady, New York, May 1971.

"Exoskeleton Prototype Project.", Final Report on Phase 1, Contract N00014-66-C0051, Prepared by General Electric Company. Schenectady, New York, Oct. 1966.

Mosher, R.S. "Handyman to Hardiman." Automotive Engineering Congress, Society of Automotive Engineers, Detroit, Michigan, Jan. 1967.

Arroyo, P. "Design of a Minimally Actuated Assistive Walking Device." Graduate Thesis, UC-Berkeley Mechanical Enoineering Dept., 1998.

Rehnmark, F. L. "Dynamic Simulation and Design of a Powered Underactuated Assistive Walking Device." Graduate Thesis, UC-Berkeley Mechanical Engineering Dept., 1997.

Walsh C.J., et al "Development of a Lightweight, Underactuated Exoskeleton for Load-carrying Augmentation." Proceedings of the 2006 IEEE International Conference on Robotics and Automation, pp. 3485-3491, Orlando, Florida, May 2006.

Croshaw, P.F. "Hardimian I Arm Test: Hardiman I Prototype Project." General Electric Company, Schenectady, New York, Jul. 1969.

Dollar, A.M., et al. "Lower-Extremity Exoskeletons and Active Orthoses: Challenges and State of the Art." IEEE Transactions on Robotics, vol. 24, No. 1, pp. 144-158, Feb. 2008.

Walsh, C.J., et al. "An Autonomous, Underactuated Exoskeleton for Load-carrying Augmentation." Proceedings of the 2006 IEEE/RSJ International Conference on Intelligent Robots and Systems, pp. 1410-1415, Beijing, China, Oct. 2006.

Kazerooni, H., et al. "On the Control of Berkeley Lower Extremity Exoskeleton (BLEEX)," Proc. of IEEE International Conference on Robotics and Automation, Barcelona, pp. 4364-4371, Spain, Apr. 2005.

Endo. K., et al, "A Quasi-passive Model of Human Leg Function in Level-ground Walking." Proceedings of the 2006 IEEE/RSJ International Conference on Intelligent Robots and Systems, pp. 4935-4939, Beijing, China, Oct. 2006.

(56) References Cited

OTHER PUBLICATIONS

Agrawal, A., et al. "Design of a Two Degree-of-freedom Ankle-Foot Orthosis for Robotic Rehabilitation." Proceedings of the 2005 IEEE 9th International Conference on Rehabilitation Robotics, pp. 41-44, Chicago, Illinois, Jun. 28-Jul. 1, 2005.

Bharadwaj, K., et al "Design of a Robotic Gait Trainer using Spring Over Muscle Actuators for Ankle Stroke Rehabilitation." Journal of Biomechanical Engineering. vol. 127, pp. 1009-1013, Nov. 2005.

Sawicki, G S., et al. "Powered Lower Limb Orthoses: Applications in Motor Adaptation and Rehabilitation." Proceedings of the 2005 IEEE 9th International Conference on Rehabilitation Robotics. pp. 206-211, Chicago, Illinois, Jun. 28-Jul. 1, 2005.

Ferris, D.P., el al. "An Improved Powered Ankle—foot Orthosis using Proportional Myoelectric Control." Gait & Posture, vol. 23, pp. 425-428, 2006.

Vukobratovic, M., et al. "Humanoid Robots." In The Mechanical Systems Design Handbook: Modeling, Measurement, and Control (Y. Hurmuzlu, ed). Chapter 27, CRC press, 2002.

Saito, Y., et al "Development of Externally Powered Lower Limb Orthosis with Bilateral-servo Actuator." Proceedings of the 2005 IEEE 9th International Conference on Rehabilitation Robotics. pp. 394-399. Chicago, Illinois, Jun. 28-Jul. 1, 2005.

Low, K.H., et al. "Development of NTU Wearable Exoskeleton System for Assistive Technologies." Proceedings of the IEEE International Conference on Mechatronics & Automation, pp. 1099-1106, Niagara Falls, Canada. Jul. 2005.

Liu, X., et al. "Development of a Lower Extremity Exoskeleton for Human Performance Enhancement." Proceedings of IEEEIRSJ International Conference on Intelligent Robots and Systems, pp. 3889-3894, Sendai, Japan, Sep. 28-Oct. 2, 2004.

Walsh, C.J., et al. "A Quasi-passive Leg Exoskeleton for Load-carrying Augmentation." International Journal of Humanoid Robotics, 2007.

Walsh, C.J. "Biomimetic Design of an Under-Actuated Leg Exoskeleton for Load-Carrying Augmentation." Graduate Thesis, Trinity College Dublin, Dept. of Mechanical Engineering. 2006.

Valente, A. "Design of a Quasi-Passive Parallel Leg Exoskeleton to Augment Load Carrying for Walking." Graduate Thesis. Massachusetts Institute of Technology, Dept. of Mechanical Engineering. 2005.

Ferris, D.P., et al. "Powered Lower Limb Orthoses for Gait Rehabilitation." Top Spinal Cord Injury Rehabilitation, vol. 11, No. 2, pp. 34-49, 2005.

Rabischong, E., et al. "Control and Command of a Six Degrees of Freedom Active Electrical Orthosis for Paraplegic Patient." Proceedings of IEEE International Workshop on Intelligent Robots and Systems, pp. 987-991, 1990.

Kosso, E.V. "A Minimum Enemy Exoskeleton." Proceedings of the 1973 Carnahan Conference on Electronic Prosthetics, pp. 86-89, 1973.

Kawamoto, H., et al. "Power Assist Method for HAL3 Estimating Operator's Intention Based on Motion Information." Proceedings of the 2003 IEEE International Workshap on Robot and Human Interactive Communication, pp. 67-72, Millbrae. California, Oct. 31-Nov. 2, 2003.

Hollander. K., et al, "An Efficient Robotic Tendon for Gait Assistance." Journal of Biomechanical Engineering, vol. 128, No. 5, pp. 788-791, 2006.

Jaukovic, N.D. "Active Peroneal Orthosis." Proceedings of the International Symposium on External Control of Human Extremities. pp. 13-20, 1981.

Popovic, D., et al. "Powered Hybrid Assistive System." Proceedings of the International Symposium on External Control of Human Extremities, pp. 177-186, 1990.

Durfee, W.K., et al., "Preliminary Design and Simulation of a Pneumatic, Stored-energy, Hybrid Orthosis for Gait Restoration." Proceedings of the 2004 ASME International Mechanical Engineering Congress. Anaheim, CA, Nov. 13-20, 2004.

Gregorczyk, K.N., et al. "The Effects of a Lower Body Exoskeleton Load Carriage Assistive Device on Oxygen Consumption and Kinematics during Walking with Loads." 25th Army Science Conference, Orlando, FL, Nov. 27-30, 2006.

Hesse, S., et al., "Upper and Lower Extremity Robotic Devices for Rehabilitation and for Studying Motor Control." Current Opinion in Neurology, vol. 16, No. 6, pp. 705-710, Dec. 2003.

Kawamoto, H., et al., "Power Assist Method for HAL-3 Using EMG-based Feedback Controller." Proceedings of the IEEE International Conference on Systems, Man, and Cybernetics, pp. 1648-1653, 2003.

Kazerooni, H, et al. "The Berkeley Lower Extremity Exoskeletons", ASME Journal of Dynamics Systems, Measurements and Control, V128, pp. 14-25, Mar. 2006.

Zoss A, et al. "Biomechanical Design of the Berkeley Lower Extremity Exoskeleton (BLEEX)", IEEE/ASME Transactions on Mechatronics, vol. 11, No. 2, pp. 128-138, Apr. 2006.

Kazerooni, H, et al. "That which does not stabilize, will only make us stronger" The International Journal of Robotics Research, vol. 26, No. 1, pp. 75-89, Jan. 2007.

Hill, J.W. "Hydraulically Powered Lower Limb Orthosis." In: Morecki, A. & Bianchi, K. (eds) Theory and Practice of Robots and Manipulators Proceedings of RoManSy 1986—6th CISM-IFToMM Symposium, pp. 182-192, The MIT Press, Boston, 1987.

Lazarevic, S.R., et al. "Logic Control of Partial Active Orthoses via Real Time Computing Systems," Proceedings of the International Symposium on External Control of Human Extremities, pp. 247-257, 1976.

Kuo, A.D. "Energetics of Actively Powered Locomotion Using the Simplest Walking Model." Journal of Biomechanical Engineering, vol. 124, pp. 113-120, Feb. 2002.

Donelan, J.M., et al. "Simultaneous Positive and Negative External Mechanical Work in Human Walking." Journal of Biomechanics, vol. 35, pp. 117-124, 2002.

Crowell, H.P., et al "Exoskeleton Power and Torque Requirements Based on Human Biomechanics." Army Research Laboratory, ARL-TR-2764, Nov. 2002.

Griffin, T.M., et al. "Walking in Simulated Reduced Gravity: Mechanical Energy Fluctuations and Exchange." The Journal of Applied Physiology, vol. 86, pp. 383-890, Jan. 1999.

Vukobratovic, M., et al. "New Model of Autonomous "Active Suit" for Distrophic Patients." Proceedings of the International Symposium on External Control of Human Extremities, pp. 33-42, 1981.

Rabischong, J.P., et al. "The Amoll Project" Poc 5th Int. Synposium on External Control of Human Extremeties. ETAN, Dubrovnik,Yogoslavia, 1975.

Grundman, J., et al. "Computer Control of Multi-task Exoskeleton for Paraplegics." In: Morecki, A. & Bianchi, K. (eds) Theory and Practice of Robots and Manipulators. Proceedings of RoManSy 1986—6th CISM-IFToMM Symposium, pp. 233-240, The MIT Press, Boston, MA, 1987.

Lee, S., et al, "Power Assist Control for Leg with HAL-3 Based on Virtual Torque and Impedance Adjustment." Proceedings of 2002 IEEE Conference on Systems, Man and Cybernetics, vol. 4, Oct. 6-9, 2002.

Jingere, S. et al. Energy Cost and Muscular Activity Required for Propulsion During Walking, J Applied Physiology, No. 94, pp. 1766-1772, 2003.

Anderschitz et al., *Patient-Cooperative Strategies for Robot-Aided Treadmill Training: First Experimental Results*, IEEE Transactions on Neural Systems and Rehabilitation Engineering, vol. 13, No. 3, Sep. 2005, pp. 380-394.

\* cited by examiner

DEVICE AND METHOD FOR DECREASING OXYGEN CONSUMPTION OF A PERSON DURING STEADY WALKING BY USE OF A LOAD-CARRYING EXOSKELETON

CROSS-REFERENCE TO RELATED APPLICATIONS

This application claims the benefit of U.S. Provisional Application No. 61/071,824 entitled DEVICE AND METHOD FOR DECREASING OXYGEN CONSUMPTION OF A PERSON DURING STEADY WALKING BY USE OF A LOAD-CARRYING EXOSKELETON, filed May 20, 2008.

STATEMENT REGARDING FEDERALLY SPONSORED RESEARCH OR DEVELOPMENT

This invention was made with government support under Contract No. DAAD19-01-1-0509 awarded by Defense Advanced Research Projects agency (DARPA). The government has certain rights in the invention.

BACKGROUND OF THE INVENTION

1. Field of the Invention

The present invention relates generally to the field of lower extremity exoskeletons and, more specifically, to the field of lower extremity exoskeletons that decrease their wearer's oxygen consumption and heart rate.

2. Discussion of the Prior Art

In a wide variety of situations, people of ordinary ability often consume a great deal of oxygen when walking or carrying a load. Certainly, the oxygen consumption and heart rate of a person will vary depending on the amount of physical exertion. In a paper entitled "A QUASI-PASSIVE LEG EXOSKELETON FOR LOAD-CARRYING AUGMENTATION", International Journal of Humanoid Robotics, 2007, the authors claim to have developed a quasi-passive exoskeleton that increases the walking metabolic cost of transport (COT), as compared to a standard loaded backpack by 10%, while further stating that a similar exoskeleton without joint springs or damping control (zero-impedance exoskeleton) was found to increase the COT by 23%, compared to the standard loaded backpack.

The provision of a quasi-passive exoskeleton, as disclosed in the prior art, is considered to negatively affect certain cardio and other physiological parameters of a user. Therefore, opportunities still exist to provide a compact, easy-to-operate, fast, and general purpose exoskeleton device, particularly such an exoskeleton device that will significantly decrease a person's oxygen consumption and heart rate while the device is being worn.

SUMMARY OF THE INVENTION

The opportunities described above are addressed in several embodiments of a lower extremity exoskeleton, wearable by a person. The lower extremity exoskeleton described here is configurable to be coupled to a person and, among other components, comprises: two leg supports configurable to be coupled to the person's lower limbs; two knee joints, each of which is configured to allow flexion and extension between a respective shank link and a respective thigh link; an exoskeleton trunk, which is configurable to be coupled to the person's upper body and is rotatably connectable to the thigh links of the leg supports, allowing for the flexion and extension between the leg supports and the exoskeleton trunk; two hip actuators, which are configured to create torques between the exoskeleton trunk and leg supports; and at least one power unit, which is capable of providing power to the hip actuators, among other components.

In operation, the exoskeleton of the present invention is utilized to reduce the oxygen consumption and heart rate of a wearer while walking. More specifically, a user is coupled to the exoskeleton such that the left and right (first and second) leg supports are attached to the wearer's lower limbs and the wearer's upper body is attached to the exoskeleton trunk. When the first leg support in a swing phase strikes the ground and enters a stance phase, the hip actuator of the first leg support rapidly creates a first unidirectional torque acting to move the first exoskeleton leg backwardly relative to the exoskeleton trunk. This first unidirectional torque pushes the exoskeleton trunk forward until the second leg support strikes the ground and enters the stance phase. When the second leg support enters the stance phase, the hip actuator of the second leg support rapidly creates the first, unidirectional torque and the hip actuator of the first leg support rapidly creates a second unidirectional torque acting in a direction to move the first leg support forward relative to the exoskeleton trunk until the first leg support leaves the ground and enters the swing phase. The exoskeleton device reduces the energy consumed by a person while walking as compared to a person without the exoskeleton device, thereby decreasing the person's oxygen consumption and heart rate.

BRIEF DESCRIPTION OF THE DRAWINGS

These and other features, aspects and advantages of the present invention will become better understood when the following detailed description is read with reference to the accompanying drawings, in which like characters represent like parts throughout the drawings, wherein.

DETAILED DESCRIPTION OF THE PREFERRED EMBODIMENTS

Figure 1:
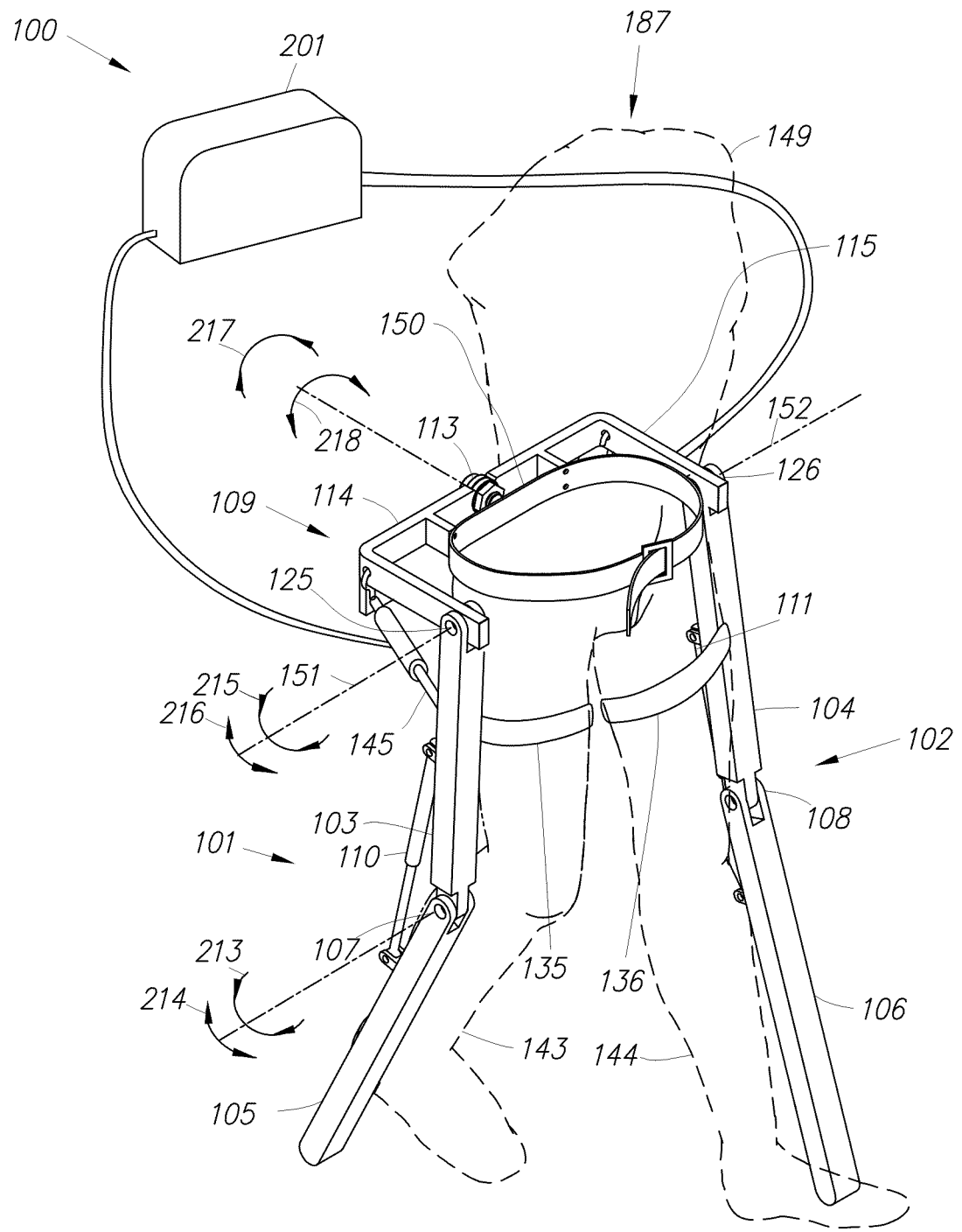
FIG. 1 is a front perspective drawing of an exoskeleton of the present invention including hip actuators.

The present invention provides for an exoskeleton device that actually decreases a wearer's oxygen consumption. In accordance with a first embodiment of the present invention, as shown in FIG. 1, a lower extremity exoskeleton 100 wearable by a person 187 is able to decrease the wearer's oxygen consumption. Lower extremity exoskeleton 100, in addition to other components, includes two leg supports 101 and 102, which are configured to be coupled to person's lower limbs 143 and 144 and configured to rest on the a support surface (e.g., the ground) during their stance phase. The term stance phase should be understood to mean the position a leg support 101 or 102 is in when a downward force is being applied to a user's foot and leg associated with the leg support 101 or 102 and the leg support 101 or 102 is in contact with the ground. The leg supports include thigh links 103 and 104 and shank links 105 and 106. Two knee joints 107 and 108 are configured to allow flexion and extension between the shank link and the thigh link of the leg supports (shown by knee flexion arrow 213 and knee extension arrow 214, respectively) during the corresponding leg support swing phase and later part of the stance phase. The term swing phase should be understood to mean the position a leg support 101 or 102 is in when a downward force is not be applied to a user's foot and leg associated with the leg support 101 or 102 and the leg support 101 or 102 is not in contact with a support surface (e.g., the ground). However, two knee joints 107 and 108 are configured to resist flexion between the shank link and the thigh link of the leg supports during the corresponding leg support stance phase. Lower extremity exoskeleton 100 further comprises an exoskeleton trunk 109. Exoskeleton trunk 109, among other components, comprises an upper body interface device 150. Exoskeleton trunk 109 is configurable to be coupled to the person's upper body 149 through upper body interface device 150. Person's upper body 149 means any location generally above the thighs, including the buttock. Examples of upper body interface device 150 include an element or combination of elements including, without limitation, vests, belts, straps, shoulder straps, chest straps, body cast, harness, and waist belts. Exoskeleton trunk 109 is rotatably connectable to leg supports 101 and 102 at hip flexion-extension joints 125 and 126, allowing for the hip flexion and extension rotations (shown by hip extension arrow 215 and hip flexion arrow 216, respectively) of leg supports 101 and 102 about hip flexion-extension axes 151 and 152, respectively. Leg supports 101 and 102 are configurable to be coupled to person's lower limbs 143 and 144 through lower limb interface straps 135 and 136.

Figure 2:
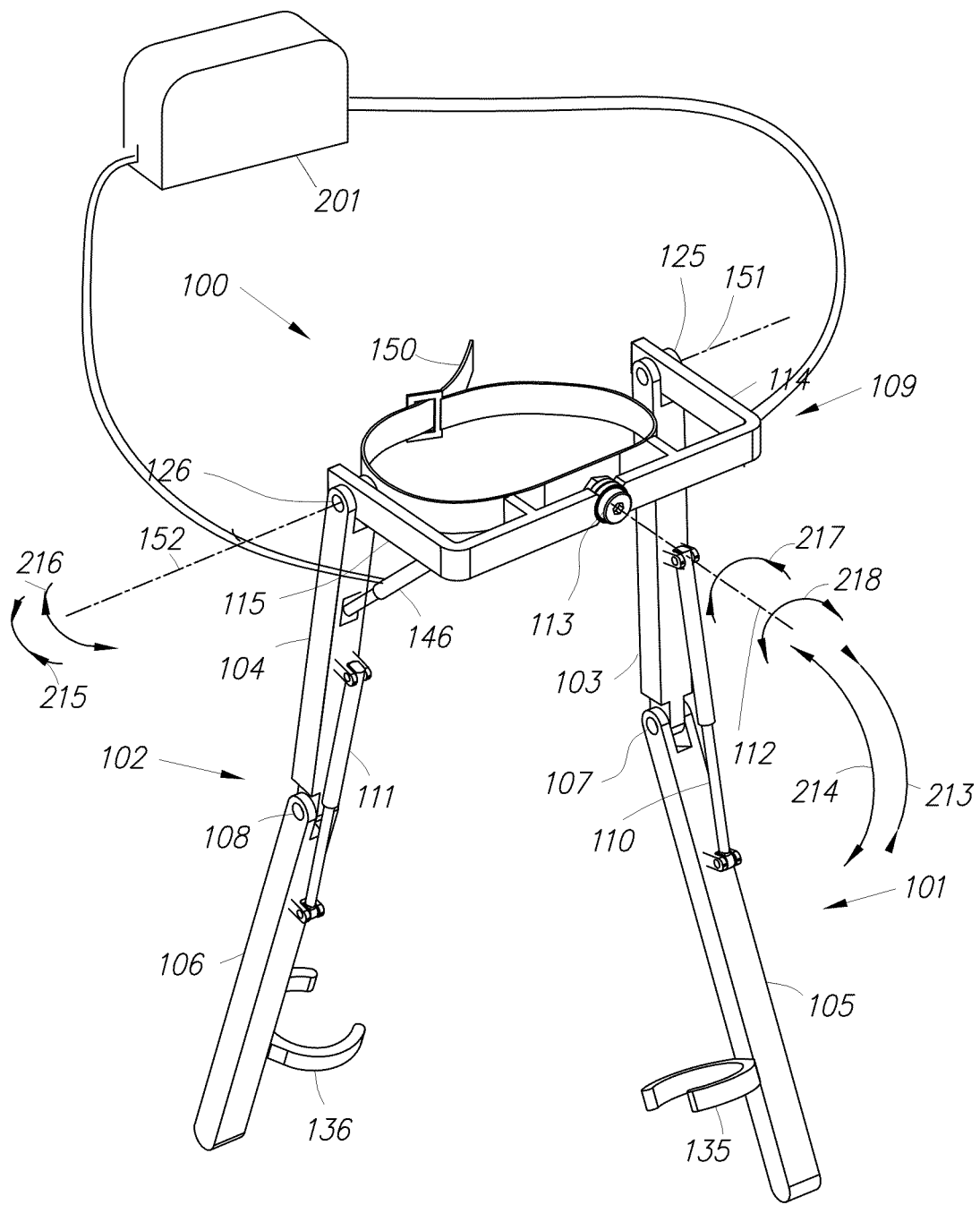
FIG. 2 is a rear perspective drawing of the exoskeleton of FIG. 1.

In some embodiments, as shown in FIG. 1, lower limb interface straps 135 and 136 are coupled to thigh links 103 and 104. In some embodiments, as shown in FIG. 2, lower limb interface straps 135 and 136 are coupled to shank links 105 and 106. In some embodiments, lower limb interface straps are coupled to both shank links and thigh links. Each lower limb interface strap 135 and 136 comprises an element or combination of elements including, without limitation, straps, bars, c-shaped brackets, body cast, and elastomers. In operation, person 187 couples to (or wears) lower extremity exoskeleton 100 through upper body interface device 150 (a simple belt in the case of FIG. 1) and by coupling to two leg supports 101 and 102 through lower limb interface straps 135 and 136. Lower extremity exoskeleton 100, among other things, further comprises two hip actuators 145 and 146, which are configured to create torques between exoskeleton trunk 109 and leg supports 101 and 102. Right hip actuator 145 is shown in FIG. 1 and left hip actuator 146 is shown in FIG. 2. Lower extremity exoskeleton 100, among other components, further comprises at least one power unit 201 capable of providing power and coupled to hip actuators 145 and 146. In some embodiments, only one power unit 201 provides power to hip actuators 145 and 146. In some embodiments, each hip actuator receives power from separate power units. Rip actuators 145 and 146 comprise any device or combination of devices capable of providing torque. Examples of hip actuators 145 and 146 include, without limitation, electric motors, including, without limitation, AC (alternating current) motors, brush-type DC (direct current) motors, brushless DC motors, electronically commutated motors (ECMs), stepping motors, hydraulic actuators, and pneumatic actuators and combinations thereof. In some embodiments, hip actuators 145 and 146 are powered by compressed gas. In some embodiments, exoskeleton trunk 109 is configured to hold a rear load behind person 187.

Figure 3:
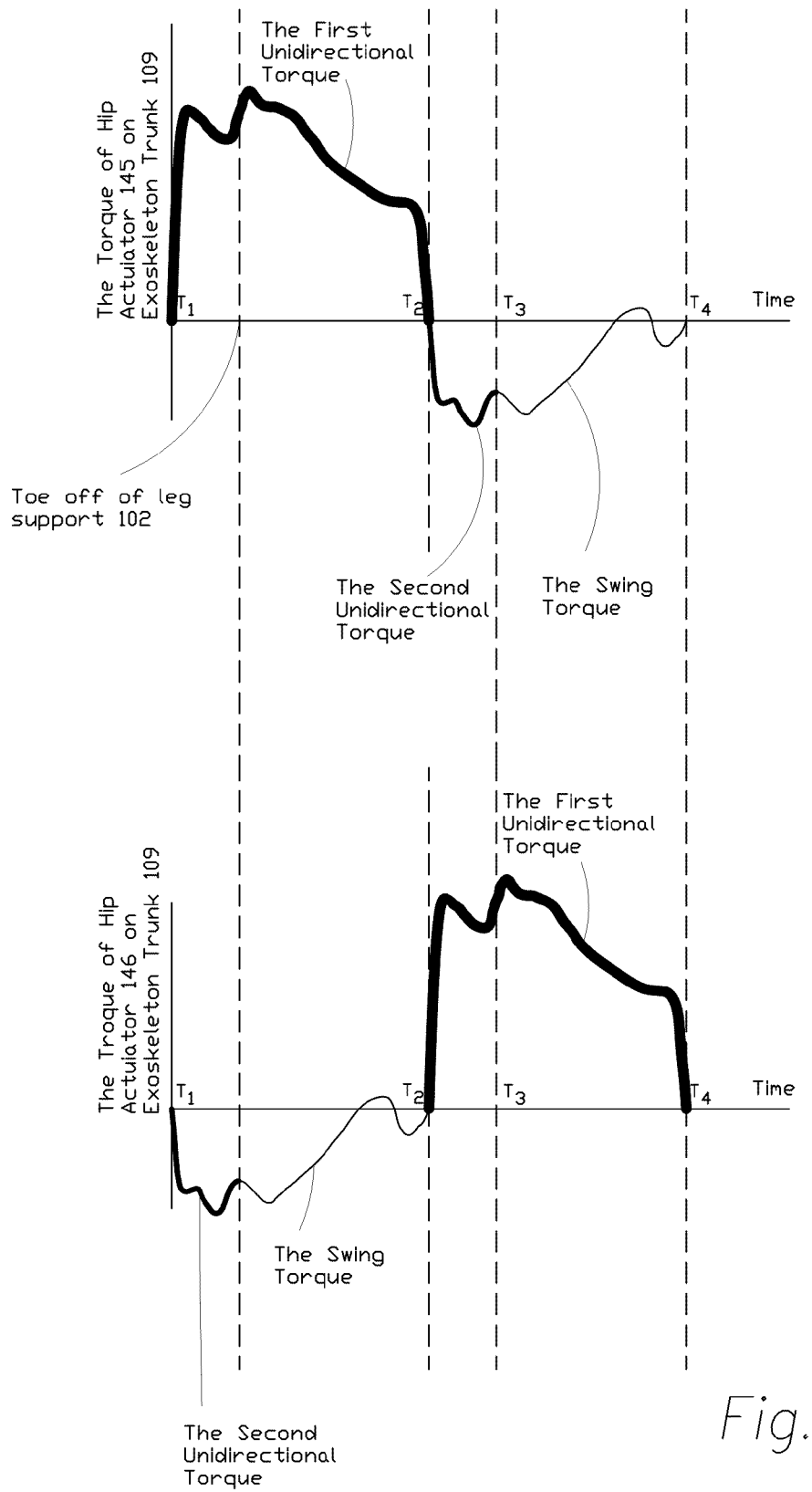
FIG. 3 is a diagram of torque profiles for the hip actuators of FIG. 1 during a walking cycle.

Lower extremity exoskeleton 100 reduces its wearer's energy expenditure and oxygen consumption when the correct torques are produced by hip actuators 145 and 146. The operation of lower extremity exoskeleton 100 can best be described by inspection of FIG. 3. FIG. 3 shows the torque being imposed by hip actuators 145 and 146 on exoskeleton trunk 109 during a walking cycle, where T1 and T2 represent the instances where right leg support 101 and left leg support 102 strike ground 130, respectively. In operation, when lower extremity exoskeleton 100 is worn by person 187 and right leg support 101 strikes ground 130 in front of left leg support 102 and enters the stance phase (i.e., Time $T_1$), power unit 201 causes hip actuator 145 of right leg support 101 to create a first unidirectional torque acting to move right leg support 101 backwardly relative to exoskeleton trunk 109 until left leg support 102, which is in the swing phase, strikes ground 130 (i.e., $T_2$). In other words, this first unidirectional torque, imposed from hip actuator 145 onto exoskeleton trunk 109, is in effect during the time between $T_1$ and $T_2$. This torque pushes exoskeleton trunk 109 in the forward velocity direction while right leg support 101 is on ground 130. Sufficiently large values for this first unidirectional torque will reduce the wearer's effort and consequently reduce the wearer's energy expenditure and oxygen consumption. $T_3$ represents the time where right leg support 101 leaves ground 130 and enters its swing phase. The time between $T_2$ and $T_3$ is called double stance in this document since both leg supports are in the stance phase.

When left leg support 102 strikes ground 130, power unit 201 performs two operations: 1) it causes hip actuator 146 of left leg support 102 to create the same first unidirectional torque which acts to move left leg support 102 backwardly relative to exoskeleton trunk 109 (this torque pushes exoskeleton trunk 109 forward when left leg support 102 is on the ground), and 2) it forces hip actuator 145 to create a second unidirectional torque acting in a direction to move right leg support 101 forward relative to exoskeleton trunk 109. This second unidirectional torque is in effect until right leg support 101 leaves ground 130 (i.e., $T_3$). $T_4$ represents the time where right leg, support 101 strikes ground 130 again and re-enters its stance phase. In some embodiments, after $T_3$ and before $T_4$ where only leg support 130 is in contact with ground 130, power unit 201 causes hip actuator 145 of right leg support 101 to create a swing torque acting in a direction to move said right leg support 101 forward relative to exoskeleton trunk 109. Sufficiently large values for this swing torque will reduce the wearer's effort in swinging her/his leg and consequently will reduce the wearer's energy expenditure and oxygen consumption. As can be seen in FIG. 3, the torque of hip actuator 146 is the same as the torque of hip actuator 145, but shifted in time.

Since the second unidirectional torque is in effect during double stance only (between $T_2$ and $T_3$), the total torque from both hip actuators 145 and 146 applied to exoskeleton trunk 109 during the double stance phase will be equal to the algebraic addition of both the first and the second unidirectional torques. In some embodiments of the invention, the magnitude of the second unidirectional torque is generally smaller than the magnitude of the first unidirectional torque. This ensures that, during the double stance phase, the total torque from hip actuators 145 and 146 to exoskeleton trunk 109 is unidirectional, pushing exoskeleton trunk 109 and person 187 forward.

Figure 4:
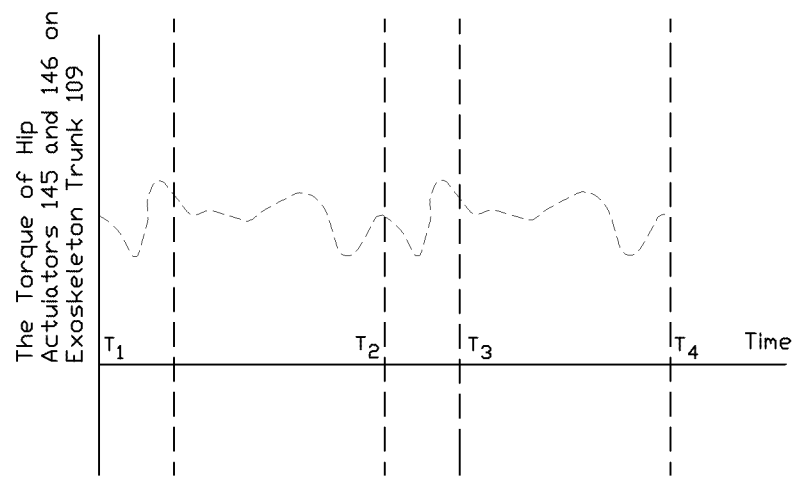
FIG. 4 is a chart of the total torque of the hip actuators of FIG. 1 over time during a walking cycle.

FIG. 4 shows the total torque being imposed by hip actuators 145 and 146 on exoskeleton trunk 109 over a walking cycle. This torque is unidirectional throughout the walking cycle, which results in pushing exoskeleton trunk 109 and person 187 forward and allows stable walking. In other words, the sum of the torques from hip actuators 145 and 146 onto exoskeleton trunk 109 acts in the direction of hip extension at all times. This results in less energy expenditure by person 187. Less energy consumption results in less oxygen consumption.

In some embodiments of the invention, the sum of the torques from hip actuators 145 and 146 onto exoskeleton trunk 109 is generally constant. In some embodiments of the invention, the sum of the torques from hip actuators 145 and 146 onto exoskeleton trunk 109 drops to no less than 50% of its maximum value at any time, and preferably drops to no less than 30% of its maximum value at any time. The maximum value should be understood as the maximum torque from hip actuators 145 and 146 applied to exoskeleton trunk 109 at any time during forward motion of the exoskeleton. This ensures that the user can walk comfortably without large torque variation on exoskeleton trunk 109 and person's upper body 149.

In some embodiments of the invention, the second unidirectional torque is zero. This means that when a leg support strikes the ground, the hip actuator of the opposite leg support that had already been on the ground creates no more torque. For example, if right leg support 101 is in its stance phase and left leg support 102 strikes ground 130, hip actuator 145 of right leg support 101 will stop imposing torque.

In some embodiments of the invention, the first unidirectional torque is generally constant, which can result in greater user comfort. In some embodiments of the invention, the second unidirectional torque is generally constant, which can result in greater user comfort. In some embodiments of the invention, the first unidirectional torque generally decreases in value during the single stance phase (when only one leg support is in the stance phase), which results in greater user comfort.

Figure 5:
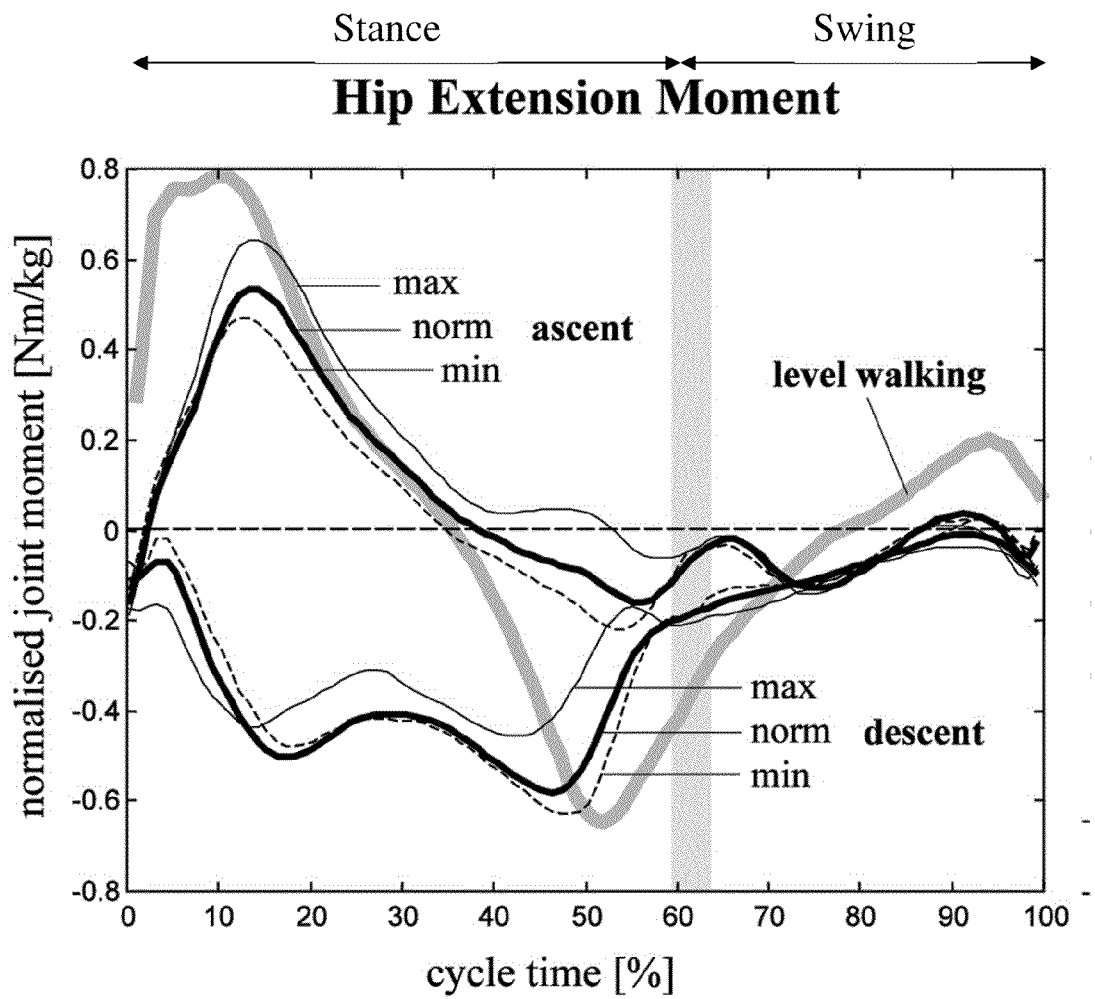
FIG. 5 is a chart of human hip torque (joint movement relative to percent cycle time) during a hip extension movement.

It is important to note that biomechanics teaches that the human hip torque during the stance phase is bidirectional. FIG. 5 shows experimentally measured human hip torque taken from the literature below, incorporated herein by reference:

"Stair ascent and descent at different inclinations", Robert Riener, Marco Rabuffetti, Carlo Frigo, *Gait and Posture*, Volume 15 Issue 1, Pages 32-44 (February 2002).

More specifically, FIG. 5 illustrates that human hip torque is positive during early stance, but becomes negative during the stance phase, changing its direction. The present invention preferably provides for a hip torque that is completely unidirectional during the stance phase, which has been determined empirically to produce the desired effect of reducing oxygen consumption.

In some embodiments of the invention, swing torque is unidirectional during the swing phase, swinging the leg support forward. To save power, in some embodiments of the invention, swing torque is zero.

In some embodiments of the invention, the swing torque is proportional to the angular velocity of swinging leg support (either with respect to exoskeleton trunk 109 or ground 130) and acts in a direction which magnifies the angular velocity of the swinging leg support. In general, if leg support 101 is in swing phase, the swing torque may be generated through the summation of any of several terms, including: a torque proportional to the angular velocity of leg support 101 in a direction that increases the angular velocity of leg support 101; a torque proportional to the angular acceleration of leg support 101 in a direction that increases the angular acceleration, of leg support 101 (either with respect to exoskeleton trunk 109 or ground 130); and a torque proportional to the sine of the hip angle of leg support 101, which acts in a direction to generally counteract the torque imposed on leg support 101 due to gravity. For example, if hip actuator 145 of leg support 101 is configured to create a swing torque that includes a torque proportional to the sine of the hip angle of leg support 101 and acts in a direction to generally counteract the torque imposed on leg support 101 due to gravity, then the wearer will supply little or no torque on leg support 101 to lift the exoskeleton leg 101 in a static sense. In a similar example, if hip actuator 145 of leg support 101 is configured to create a swing torque proportional to the angular acceleration of leg support 101 (either with respect to exoskeleton trunk 109 or ground 130) in a direction that increases the angular acceleration of leg support 101, then the effective inertia of leg support 101 is reduced and leg support 101 becomes easier to accelerate (feels lighter), which is particularly beneficial during early swing, when the swing leg must accelerate quickly. Of course, if the constant of proportionality between the measurement and the torque is chosen to be too large, leg support 101 in the swing phase will become unstable. In practice, it has been found to be best to experimentally determine an appropriate constant of proportionality.

In some embodiments of the invention, the magnitude of the swing torque generally decreases over the period of swing to allow the leg to decelerate naturally at the end of swing. The period of the swing should be understood to mean the time the leg is in the swing phase starting with early swing, passing through a mid point of the swing and ending in late swing. In some embodiments of the invention, the swing torque is near zero in late swing. In some embodiments of the invention, the swing torque magnitude decreases over the period of swing until swing torque switches direction in late swing.

In some embodiments of the invention, when right leg support 101 is in the single stance phase (e.g., left leg support 102 is in the swing phase) the first unidirectional torque may be a summation which includes a component proportional to the negative of the swing torque being generated by hip actuator 146 of leg support 102. In some embodiments, this component will be equal to the negative of the swing torque being generated by hip actuator 146 of leg support 102.

Figure 6:
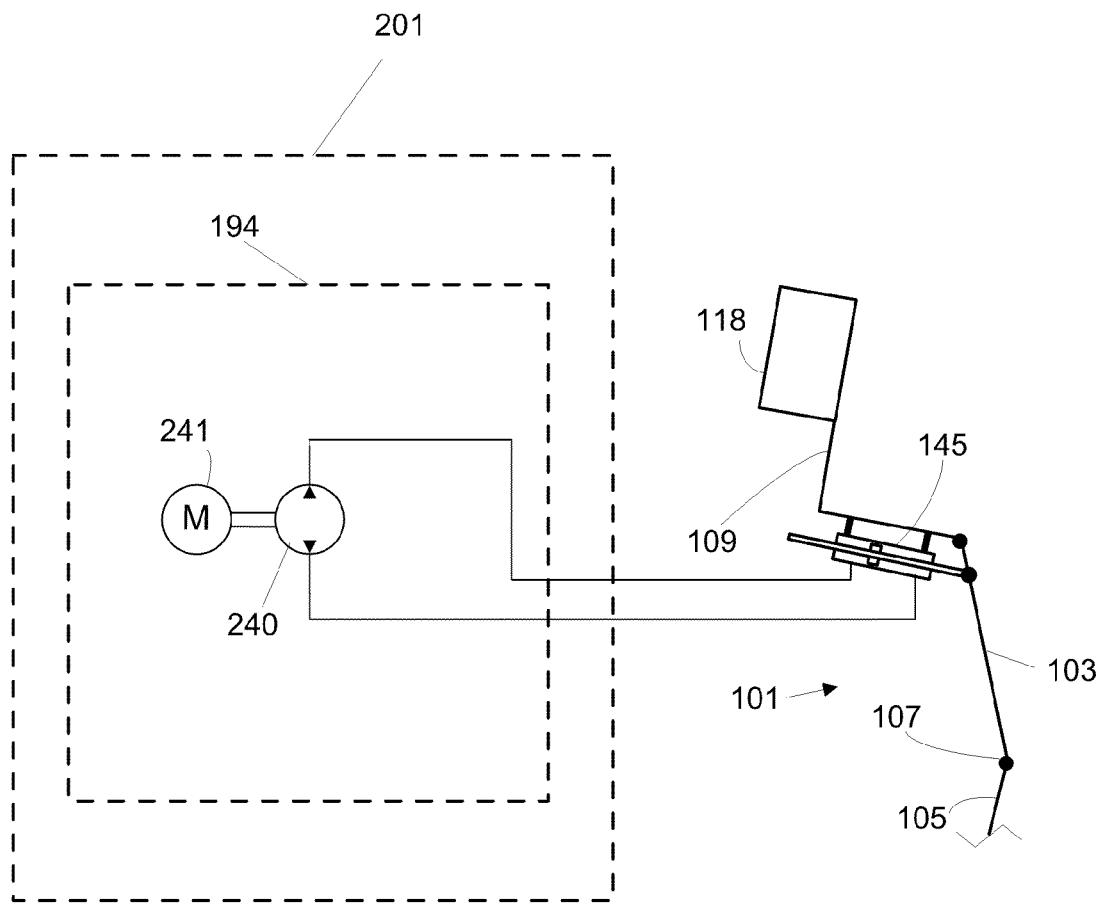
FIG. 6 is a schematic drawing of a power unit of the present invention.

In some embodiments, each of hip actuators 145 and 146 comprises a hydraulic hip actuator. In these embodiments, at least one power unit 201 provides hydraulic power to hip actuators 145 and 146. In some embodiments, only one power unit 201 provides hydraulic power to hydraulic hip actuators 145 and 146. In some embodiments, each hydraulic hip actuator receives hydraulic power from separate power units. In some embodiments, power unit 201, as shown in FIG. 6, among other components, comprises at least one hydraulic circuit 194 connectable to at least one of hydraulic hip actuators 145 and 146, and modulates the hydraulic fluid flow to and from hydraulic hip actuators 145 and 146. In some embodiments, hydraulic hip actuators 145 and 146 are hydraulic piston-cylinders. In some embodiments, hydraulic hip actuators 145 and 146 are rotary hydraulic vane type hydraulic actuators. In some embodiments, as shown in FIG. 6, hydraulic circuit 194, among other components, comprises a hydraulic pump 240 coupled to an electric motor 241.

By controlling electric motor 241, the torque profile of FIG. 3 can be implemented on hip actuators 145 and 146. Since the torque is a function of the hydraulic pressure and the hip actuator geometry, the hip actuator torque can be controlled by creating a closed loop control on the electric motor 241 by measuring the hydraulic pressure as the feedback variable. In some embodiments, the hip actuator torque can be controlled to follow the trajectory of FIG. 3 by creating a closed loop control on the electric motor 241 by measuring the hip actuator torque or force as the feedback variable.

Figure 7:
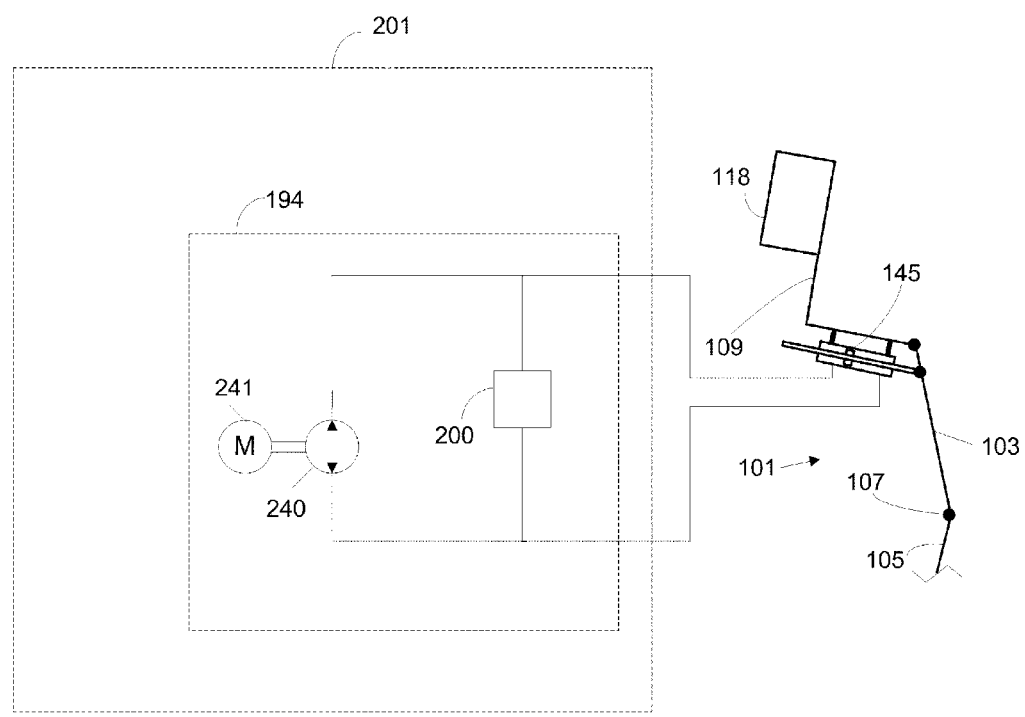
FIG. 7 is a schematic drawing of an alternative power unit of the present invention including a flow restrictive valve.

In some embodiments, as shown in FIG. 7, hydraulic circuit 194, among other components, further comprises an actuated flow restricting valve 200 capable of redirecting hydraulic fluid from hydraulic right hip actuator 145 around hydraulic pump 240. In operation, when hydraulic pump 240 is in use, actuated flow restricting valve 200 is closed. In operation, when it is necessary to reduce the power consumption, electric motor 241 will not be powered. In that case, actuated flow restricting valve 200 may be opened so that unpowered electric motor 241 and pump 240 will not impede the motion of right hip actuator 145.

Figure 8:
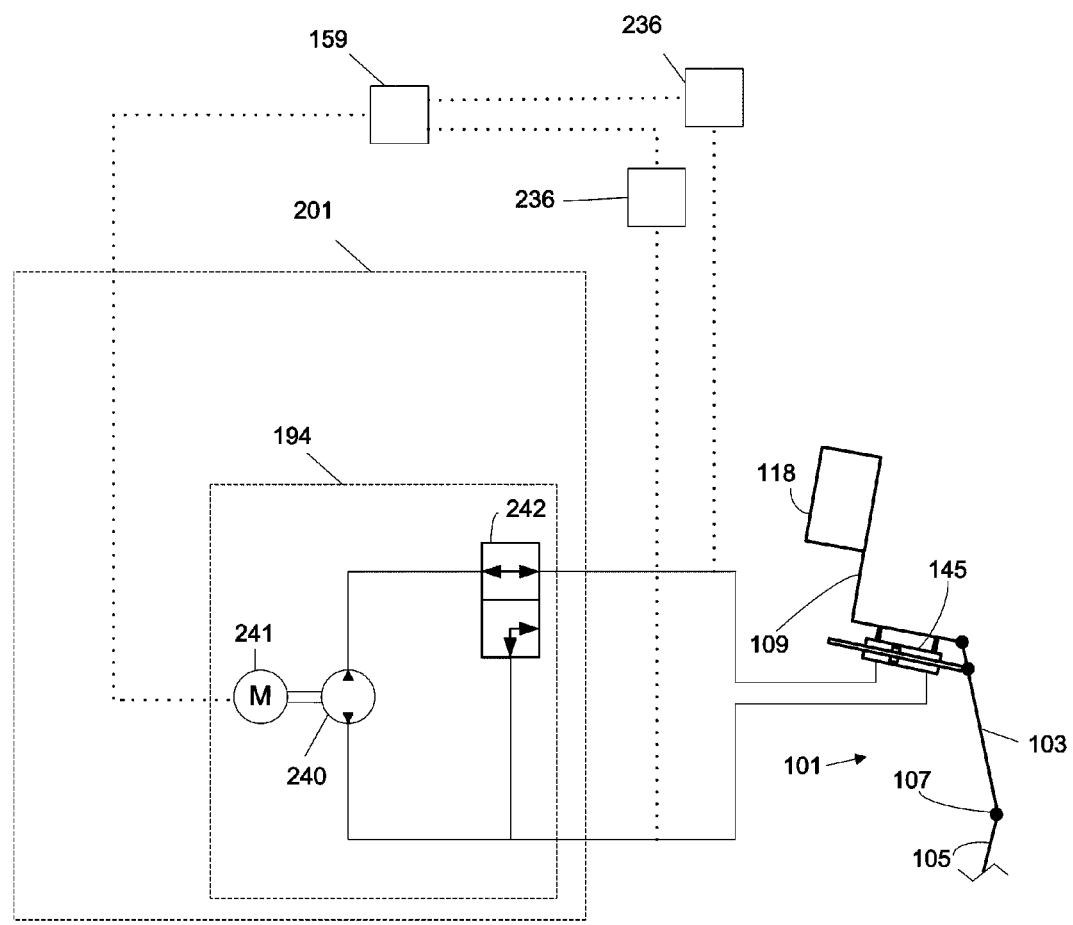
FIG. 8 is a schematic drawing of an alternative power unit of the present invention including a three-way valve.

In some embodiments, as shown in FIG. 8, hydraulic circuit 194, among other components, further comprises a three-way valve 242. In operation, while power unit 201 provides hydraulic power to right hip actuator 145, three-way valve 242 connects hydraulic right hip actuator 145 to hydraulic pump 240. In operation, when it is necessary to reduce the power consumption, electric motor 241 will not be powered. In that case, three-way valve 242 may redirect hydraulic fluid from hydraulic right hip actuator 145 around hydraulic pump 240 so that unpowered electric motor 241 and pump 240 will not impede the motion of right hip actuator 145.

Hydraulic hip actuators 145 and 146 can comprise any hydraulic actuators or combination of actuators capable of converting pressurized hydraulic fluid into force or torque. Examples of hydraulic actuators include, without limitation, linear hydraulic piston-cylinders, rotary hydraulic actuators, rack-and-pinion-type rotary actuators, and rotary hydraulic vane type actuators where pressurized hydraulic fluid, by pushing against moving surfaces, generate force or torque. Actuated flow restricting valve 200 comprises any valve or combination of valves capable of performing the indicated functions. Examples of actuated flow restricting valve 200 include, without limitation, flow control valve, pressure control valve, actuated needle valves, solenoid valves and on-off valve.

Hydraulic pump 240 comprises any pump or combination of pumps capable of performing the indicated functions. Examples of hydraulic pump 240 include, without limitation, a gear pump, vane pump, axial piston pump, and radial piston pump.

Electric motor 241 comprises any device or combination of devices capable of driving hydraulic pump 240. Examples of motor 241 include, without limitation, electric motors, including, without limitation, AC (alternating current) motors, brush-type DC (direct current) motors, brushless DC motors, electronically commutated motors (ECMs), stepping motors, and combinations thereof. Although we state that electric motor 241 turns hydraulic pump 240, one skilled in the art can realize that both motor 241 and hydraulic pump 240 may have other types of non-rotational couplings, such as reciprocating linear motion.

In some embodiments of the invention, lower extremity exoskeleton 100 comprises at least one signal processor 159 capable of controlling hip actuators 145 and 146. Signal processor 159 comprises an element or combination of elements selected from the group consisting of analog devices; analog computation modules; digital devices including, without limitation, small-, medium-, and large-scale integrated circuits, application specific integrated circuits, programmable gate arrays, programmable logic arrays; electromechanical relays, solid state switches, MOSFET switches and digital computation modules including, without limitation, microcomputers, microprocessors, microcontrollers, and programmable logic controllers. In operation, to decrease the wearer's oxygen consumption, signal processor 159 computes a torque profile that follows the torque profile shown in FIG. 3. This torque is then produced by hip actuators 145 and 146 during their respective stance phases.

In some embodiments where hip actuators 145 and 146 are hydraulic actuators, signal processor 159, by controlling electric motor 241, computes a torque profile, as shown in FIG. 3, for hip actuators 145 and 146. Since the torque is a function of the hydraulic pressure and the hip actuator geometry, the hip actuator torque, in some embodiments, as shown in FIG. 8, can be controlled by creating a closed loop control on the electric motor 241 by measuring the hydraulic pressure as the feedback variable. Pressure sensor 236 measures the pressure of the hydraulic fluid and signal processor 159 ensures the pressure is regulated to the desired value. In some embodiments, the hip actuator torque can be controlled to follow the architecture of FIG. 3 by creating a closed loop control on the electric motor 241 by measuring the hip actuator torque or force as the feedback variable.

Signal processor 159, in some embodiments, is mounted to exoskeleton trunk 109. In other embodiments, signal processor 159 is located inside power unit 201. Signal processor 159 may be a simple mechanical device constituted by, a hydraulic or pneumatic circuit or it may include electronic elements as well.

Figure 9:
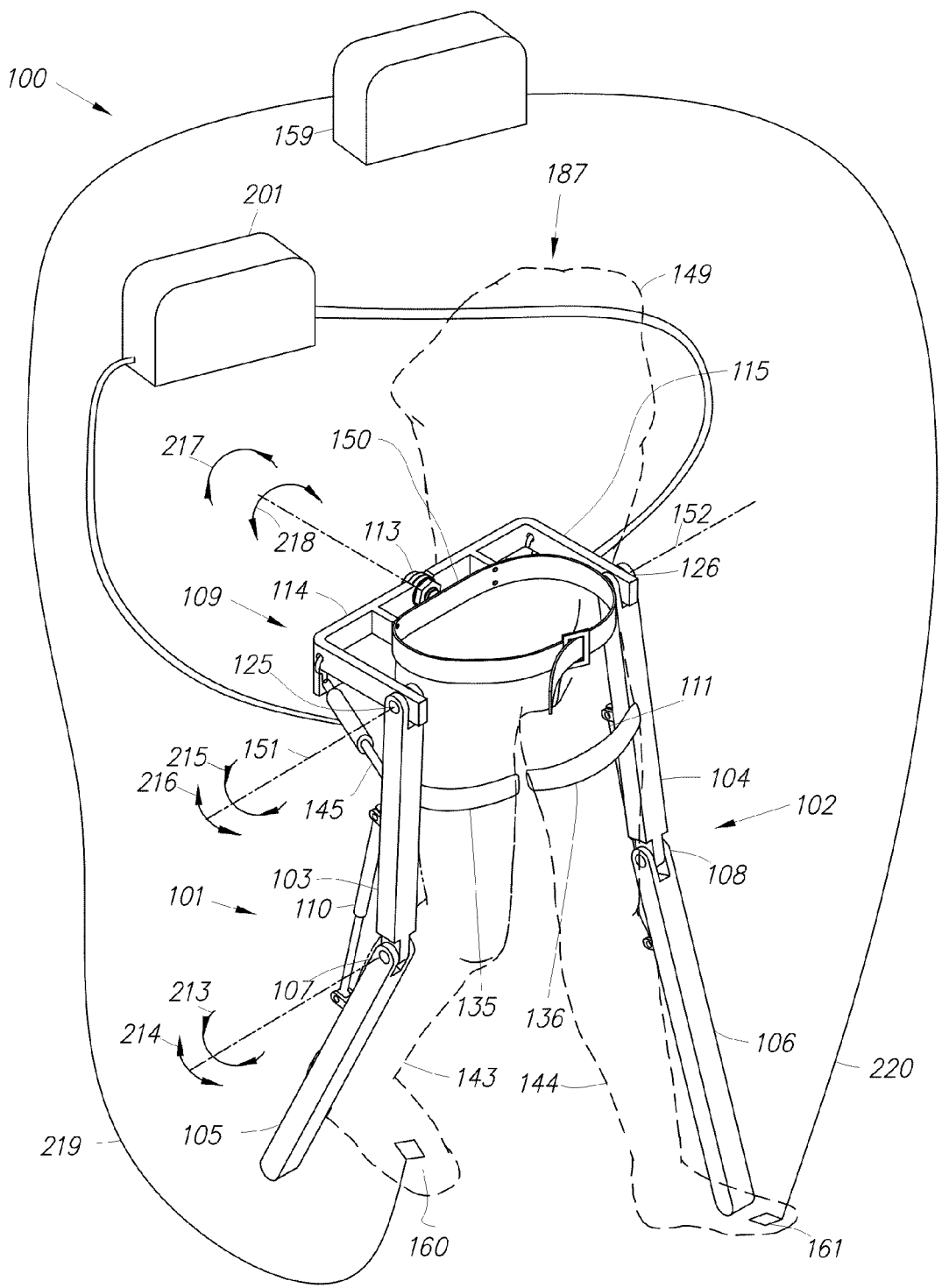
FIG. 9 is a perspective drawing of an alternative exoskeleton of the present invention including stance sensors in communication with a signal processor.

In some embodiments, as shown in FIG. 9, lower extremity exoskeleton 100 comprises at least one stance sensor per leg support, which produces a stance signal indicating whether that leg support is in, the stance phase. For instance, leg support 101 includes stance sensor 160, which produces a stance signal 219. Stance signal 219 indicates whether leg support 101 is in the stance phase. Similarly, in the embodiment of FIG. 6, leg support 102 includes stance sensor 161, which produces a stance signal 220. Stance signal 220 indicates whether leg support 102 is in the stance phase. In some embodiments, stance sensors 160 and 161 are coupled to shank links leg support 101 and 102, respectively. In operation, signal processor 159 computes a torque profile according to the shape of FIG. 3 depending on whether stance signals 219 and 220 indicate if leg supports 101 and 102 are either in the stance phase or in the swing phase. In some embodiments, stance sensors 160 and 161 are located inside the human shoe (or boot) soles. In some embodiments, stance sensors 160 and 161 are located inside the human shoes or boots. In some embodiments, stance sensors 160 and 161 are connectable to the bottom of human shoes or boots.

Further, examining the geometry of the exoskeleton shown in FIG. 1, exoskeleton trunk 109, in addition to other components, comprises two hip links 114 and 115 rotatably connectable to thigh links 103 and 104 at hip flexion-extension joints 125 and 126, allowing for the flexion and extension of leg supports 101 and 102 about hip flexion-extension axes 151 and 152, respectively. In some embodiments, hip links 114 and 115 are rotatably connected to each other at hip abduction-adduction joint 113, allowing for abduction and/or adduction of leg supports 101 and 102. Abduction and adduction of leg supports 101 and 102 are shown by arrows 217 and 218, respectively.

Figure 10:
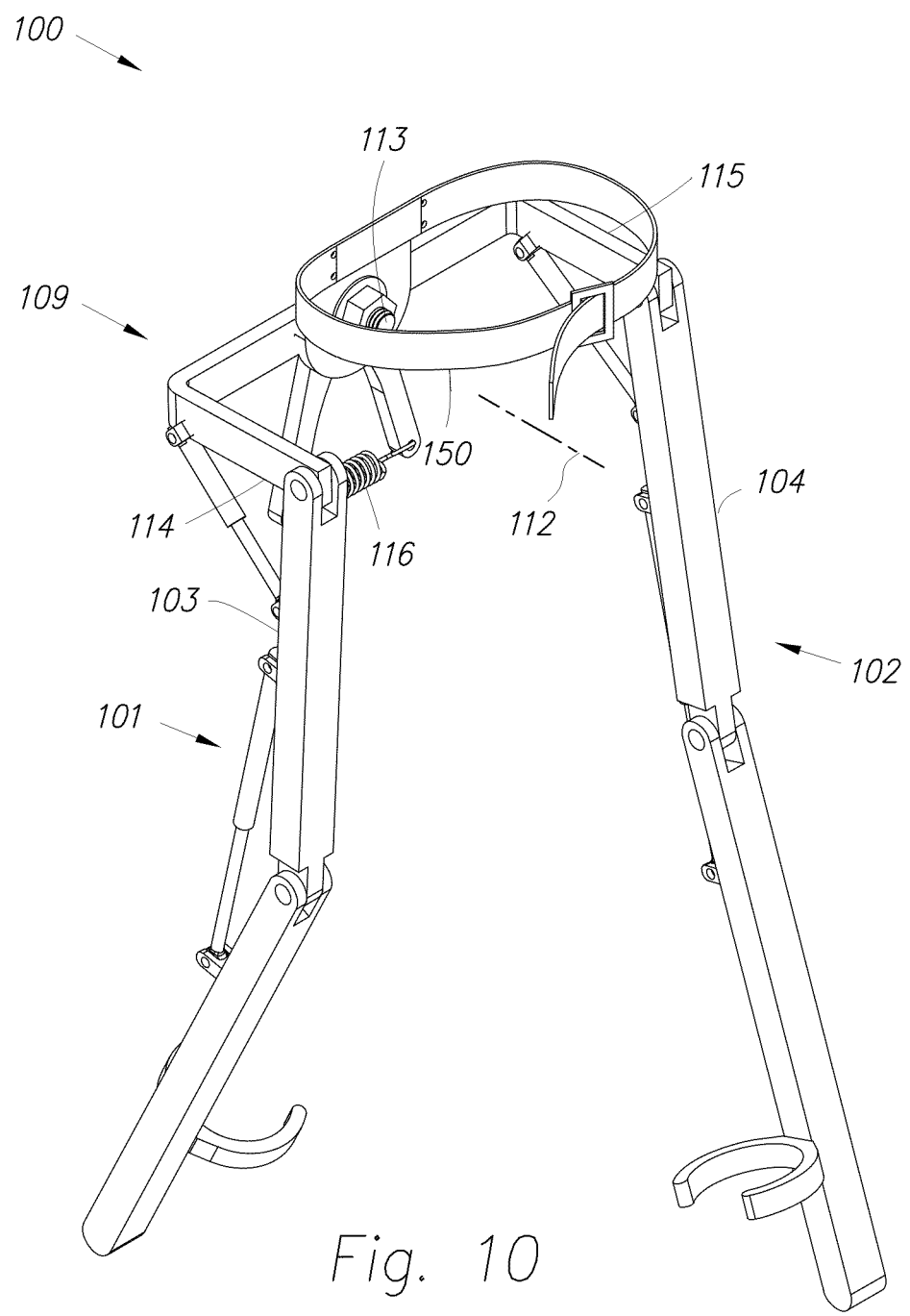
FIG. 10 is a perspective drawing of an alternative exoskeleton of the present invention including a hip resilient element.

FIG. 10 shows another embodiment of the invention where exoskeleton trunk 109 further comprises a hip resilient element 116 configured to apply a torque between hip links 114 and 115. Examples of hip resilient element include, without limitation, extension spring, compression spring, leaf spring, gas spring, air spring, rubber, elastomer, surgical tube, bungee cord and combinations thereof. The stiffness of hip resilient element 116 may be chosen such that its force generally holds up the weight of the leg supports 101 or 102 during a swing phase.

Figure 11:
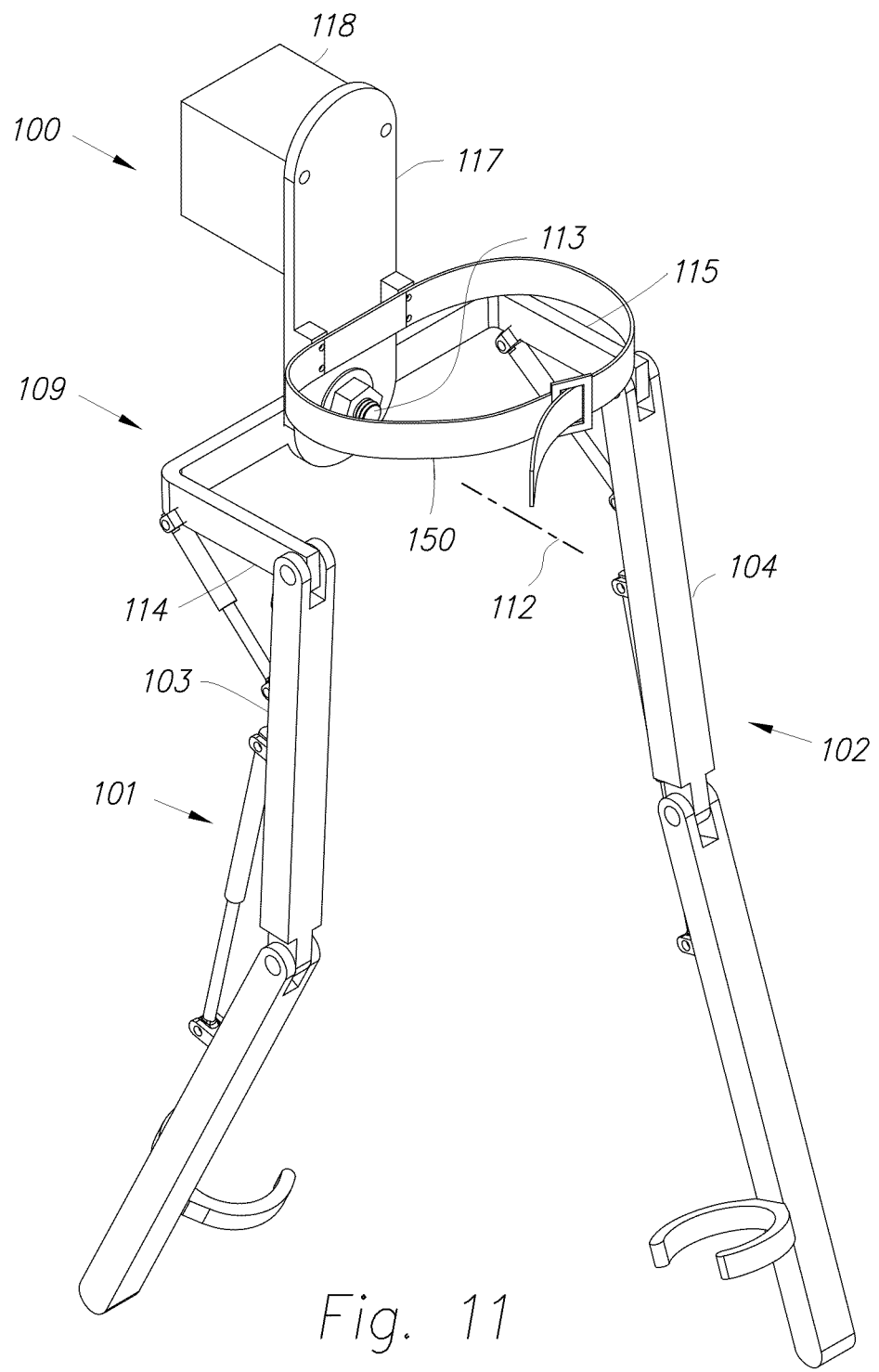
FIG. 11 is a perspective drawing of an alternative exoskeleton of the present invention including a connecting bracket for carrying a rear load.

In some embodiments, exoskeleton trunk 109 is configured to hold a rear load 118 behind person 187. FIG. 11 is a perspective drawing wherein exoskeleton trunk 109, among other components, further comprises a connecting bracket 117 configured to transfer the weight of a rear load 118 to exoskeleton trunk 109.

Figure 12:
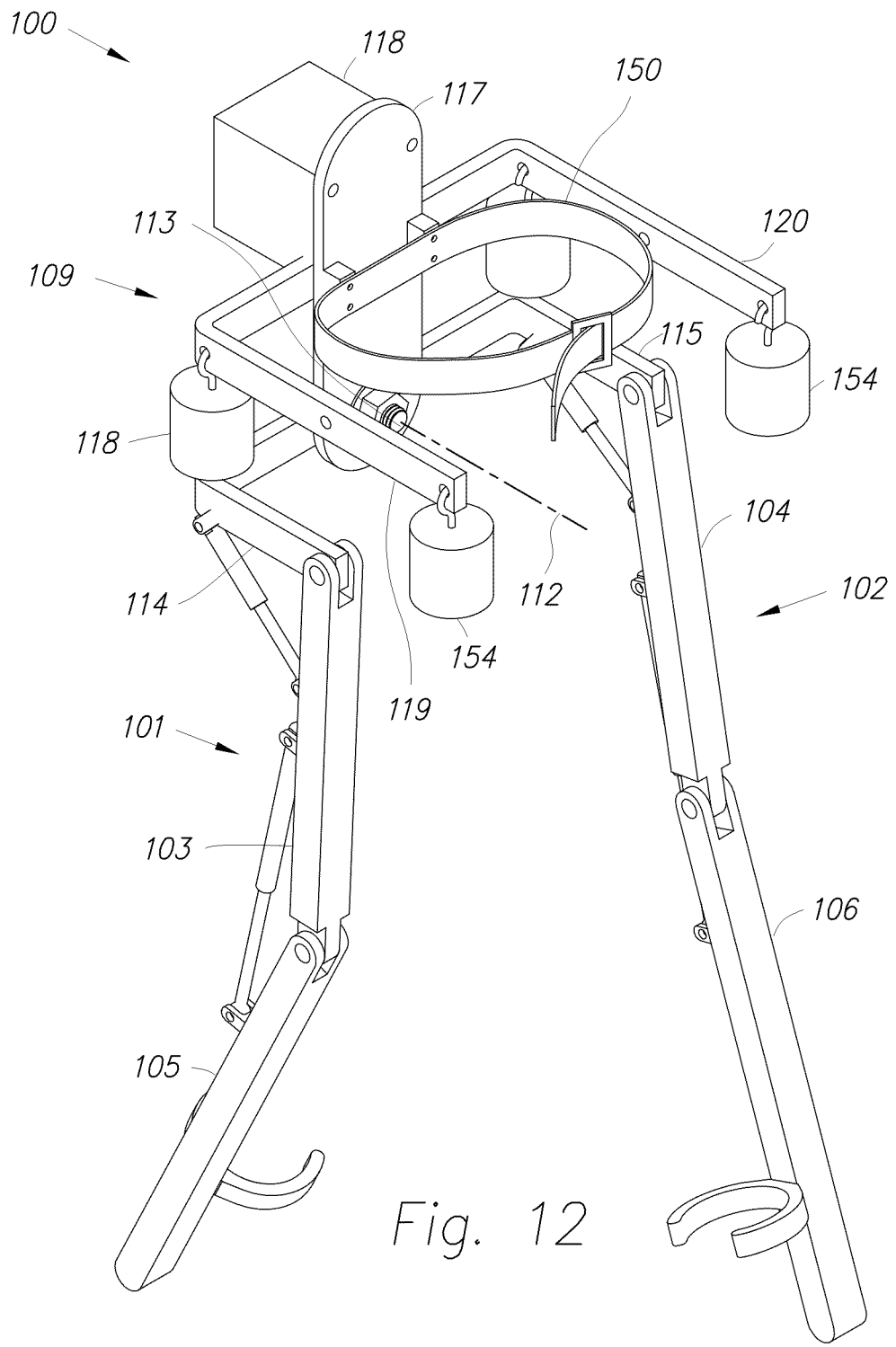
FIG. 12 is a perspective drawing of an alternative exoskeleton of the present invention including extension frames for carrying a front load.

In some embodiments, as shown in FIG. 12, connecting bracket 117 further comprises extension frames 119 and 120, configured to hold front load 154 in front of person 187. Examples of rear load 118 and front load 154 include, without limitation, backpack, baby carrier, food containers, sacks, boxes, water jugs, tool boxes, barrels, ammunition, weaponry, bedding, first aid supplies, golf bags, mail bags, camera, steadycam, leaf blower, compressor, electromechanical machineries and combinations thereof. In some embodiments, rear load 118 and/or front load 154 can be constituted by another person being carried by person 187. In some embodiments, exoskeleton trunk 109 supports a portion of the weight of person 187 through human upper body interface device 150.

Figure 13:
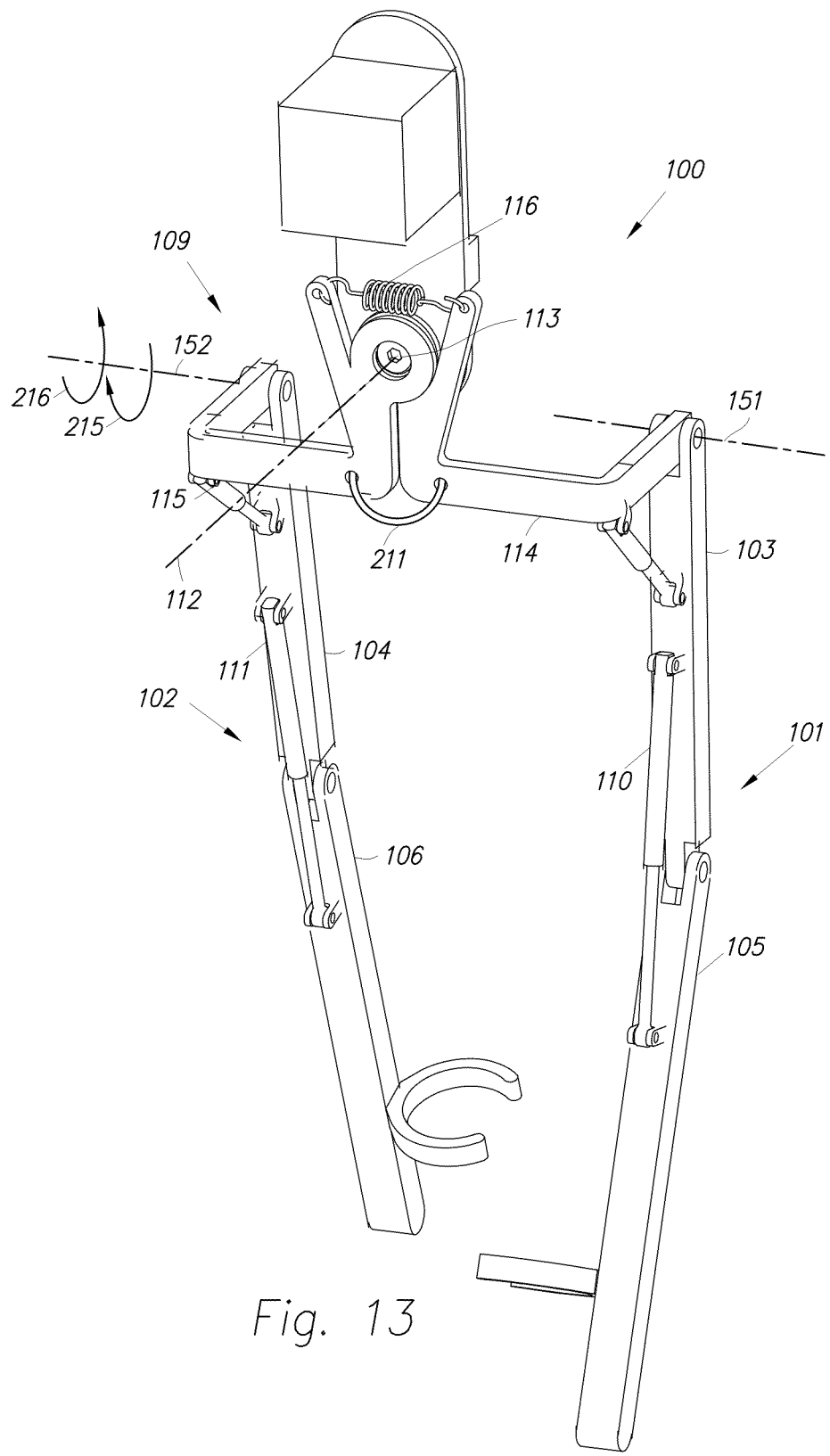
FIG. 13 is a perspective drawing of an alternative exoskeleton of the present invention including a hip abduction stop.

Some embodiments, as shown in FIG. 13, may also include a hip abduction stop 211, which limits or prevents hip links 114 and 115 from abducting with respect to each other. In the particular embodiment shown in FIG. 13, hip abduction stop 211 is created using a wire rope. Wire rope hip abduction stop 211 prevents abduction of leg supports 101 and 102 past some angle from occurring, but allows adduction of leg supports 101 and 102.

Figure 14:
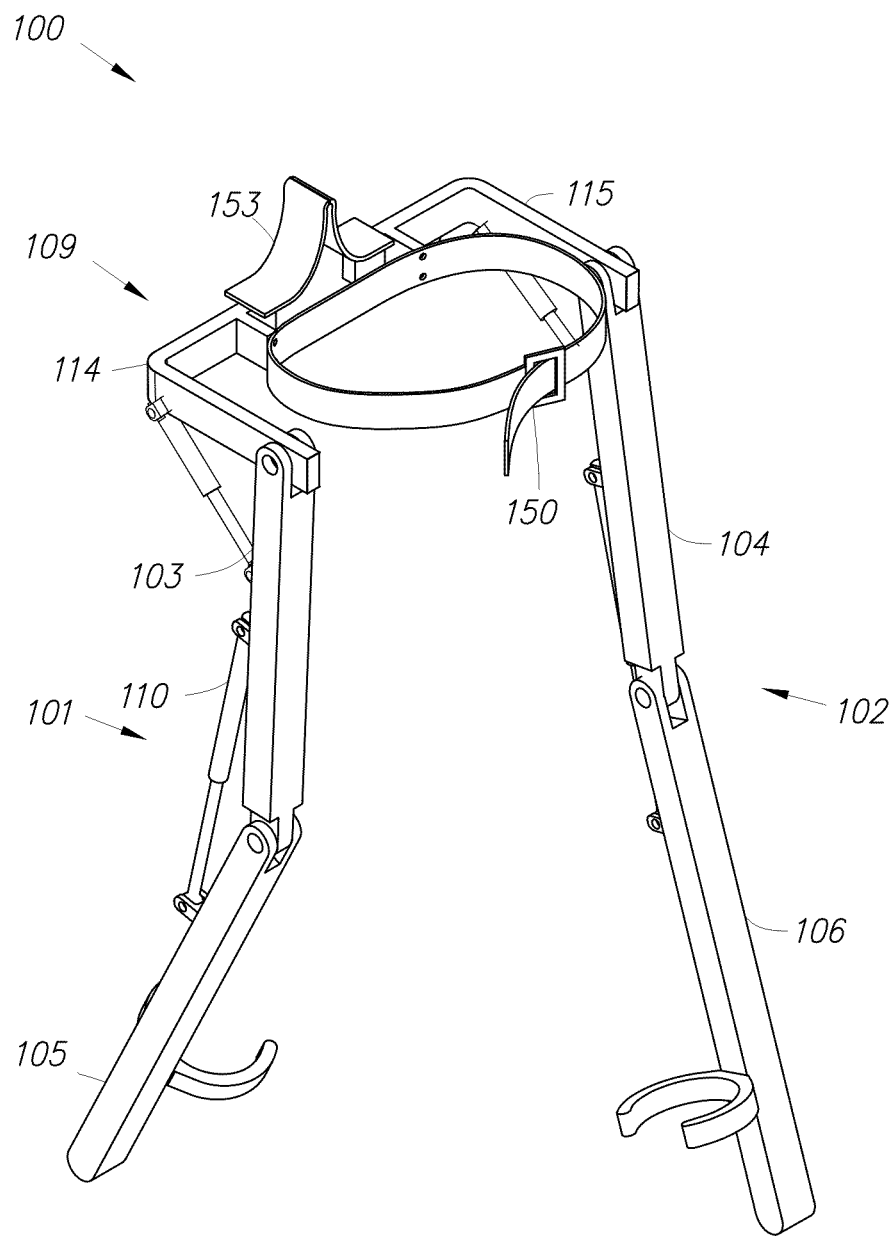
FIG. 14 is a perspective drawing of an alternative exoskeleton of the present invention including a hip resilient element in the form of a leaf spring.

In accordance with another embodiment of the invention, FIG. 14 is a perspective drawing where exoskeleton trunk 109 includes two hip links 114 and 115 rotatably connectable to thigh links 103 and 104, allowing for flexion and extension of leg supports 101 and 102 relative to exoskeleton trunk 109, wherein hip links 114 and 115 are compliantly connected to each other, allowing for abduction and/or adduction of leg supports 101 and 102. In the example shown in FIG. 14, this is accomplished by a leaf spring acting as hip resilient element 153.

Figure 15:
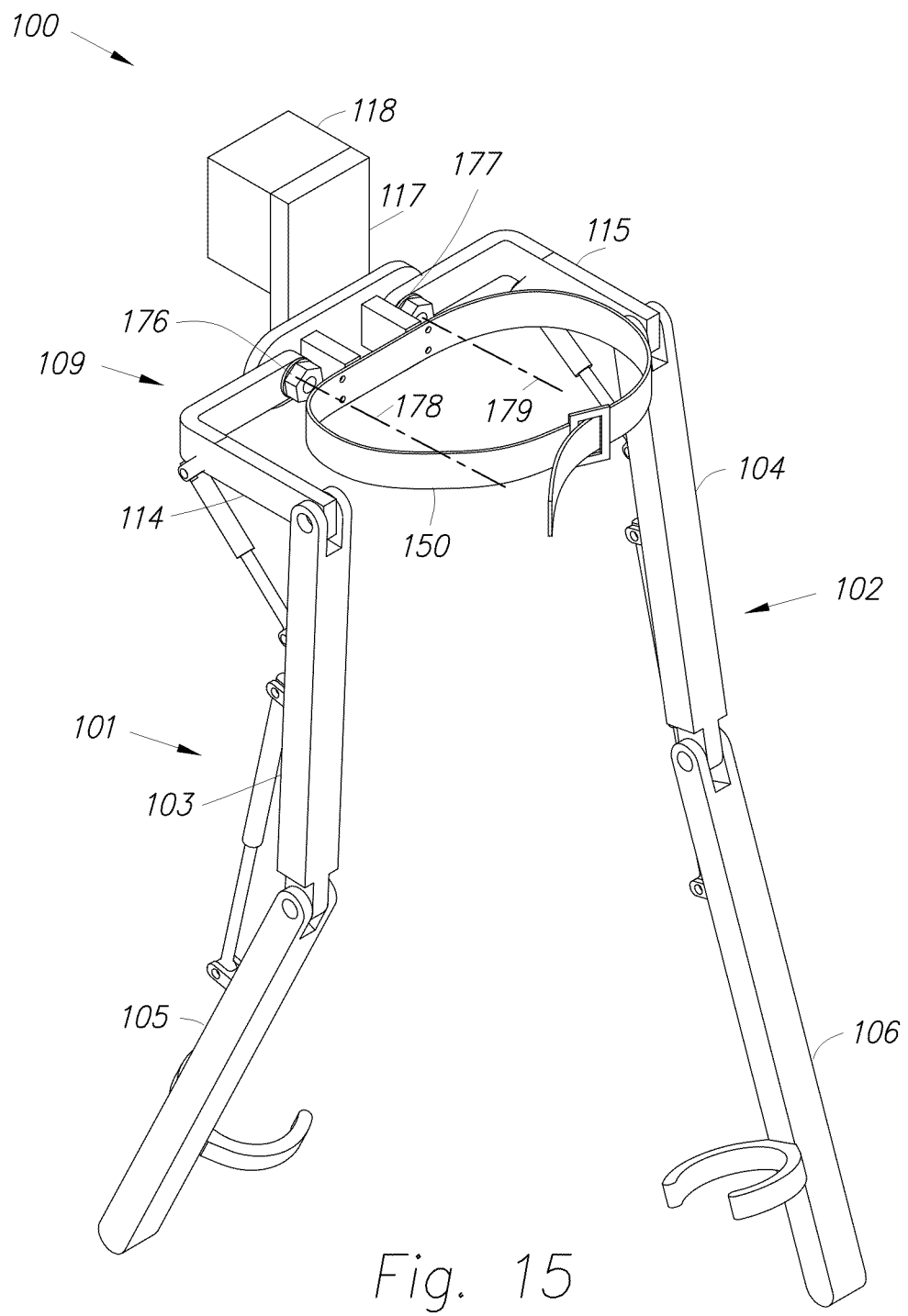
FIG. 15 is a perspective drawing of an alternative exoskeleton of the present invention including two hip resilient elements.

In accordance with another embodiment of the invention, FIG. 15 is a perspective drawing wherein exoskeleton trunk 109, among other components, further comprises a connecting bracket 117 configured to transfer the weight of a rear load 118 to exoskeleton trunk 109. Exoskeleton trunk 109 further comprises two hip links 114 and 115 rotatably connectable to thigh links 103 and 104, allowing for flexion and extension of leg supports 101 and 102 relative to exoskeleton trunk 109. Hip links 114 and 115 are rotatably connected to connecting bracket 117 via two hip abduction-adduction joints 176 and 177 and rotate about two hip abduction-adduction axes 178 and 179. In some embodiments, hip abduction-adduction axes 178 and 179 are generally parallel to each other. In some embodiments, hip abduction-adduction joints 176 and 177 coincide with each other. Furthermore, in some embodiments, as shown in FIGS. 9-12, hip abduction-adduction joints 176 and 177 coincide with each other forming hip abduction-adduction joint 113, while hip abduction-adduction axes 178 and 179 become one hip abduction-adduction axis 112.

Figure 16:
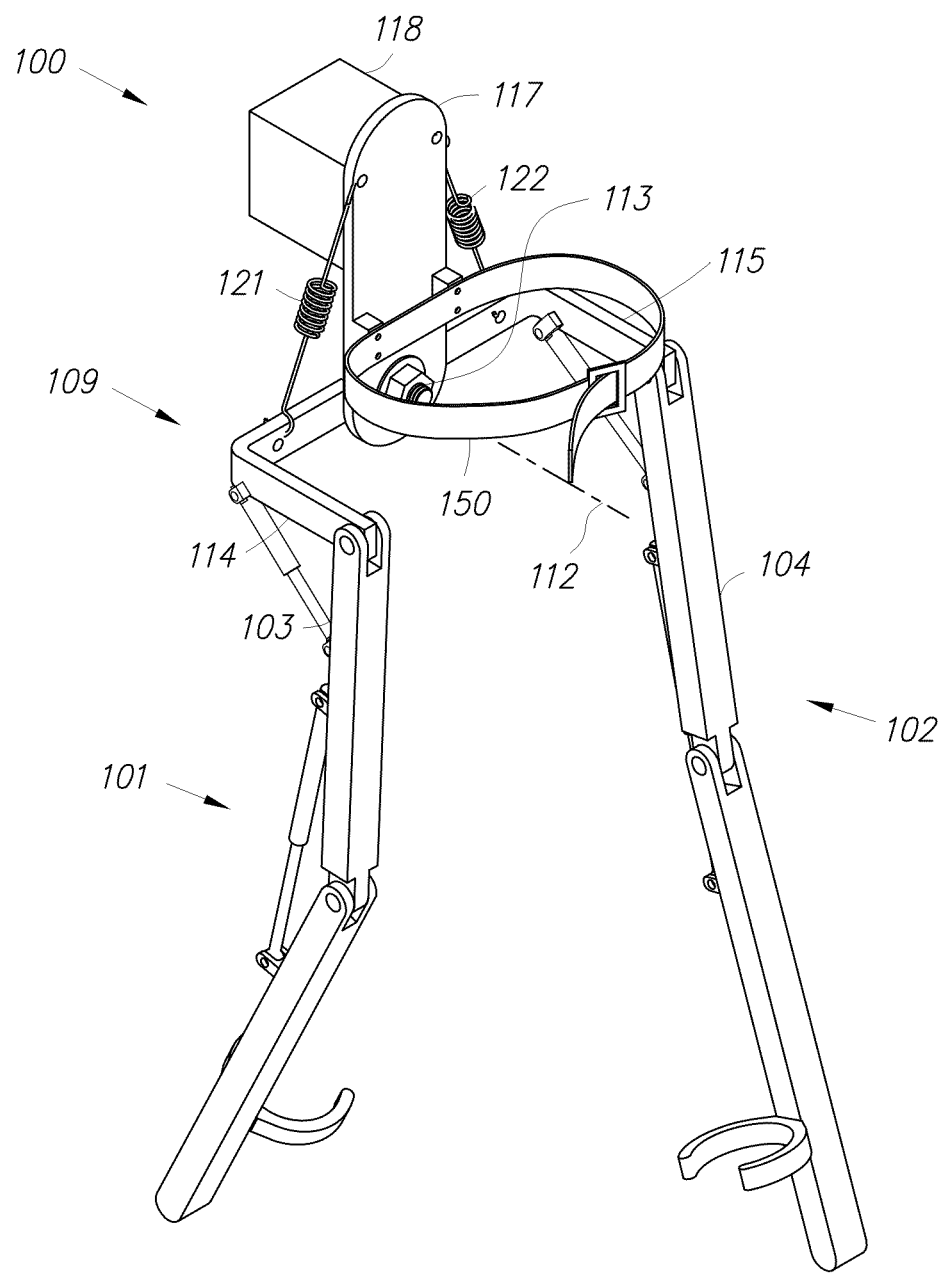
FIG. 16 is a perspective drawing of an alternative exoskeleton of the present invention including two hip joints.

In some embodiments, as shown in FIG. 16, exoskeleton trunk 109 further comprises abduction-adduction hip resilient elements 121 and 122 configured to apply torques between hip links 114 and 115 and connecting bracket 117. Examples of hip abduction-adduction resilient elements include, without limitation, extension spring, compression spring, gas spring, air spring, rubber, surgical tube, leaf spring, bungee cord and combinations thereof. The stiffness of abduction-adduction hip resilient elements 121 and 122 may be chosen such that its force generally holds up the weight of the leg supports 101 or 102 during the swing phase and aid the person in keeping the load oriented vertically while walking.

Figure 17:
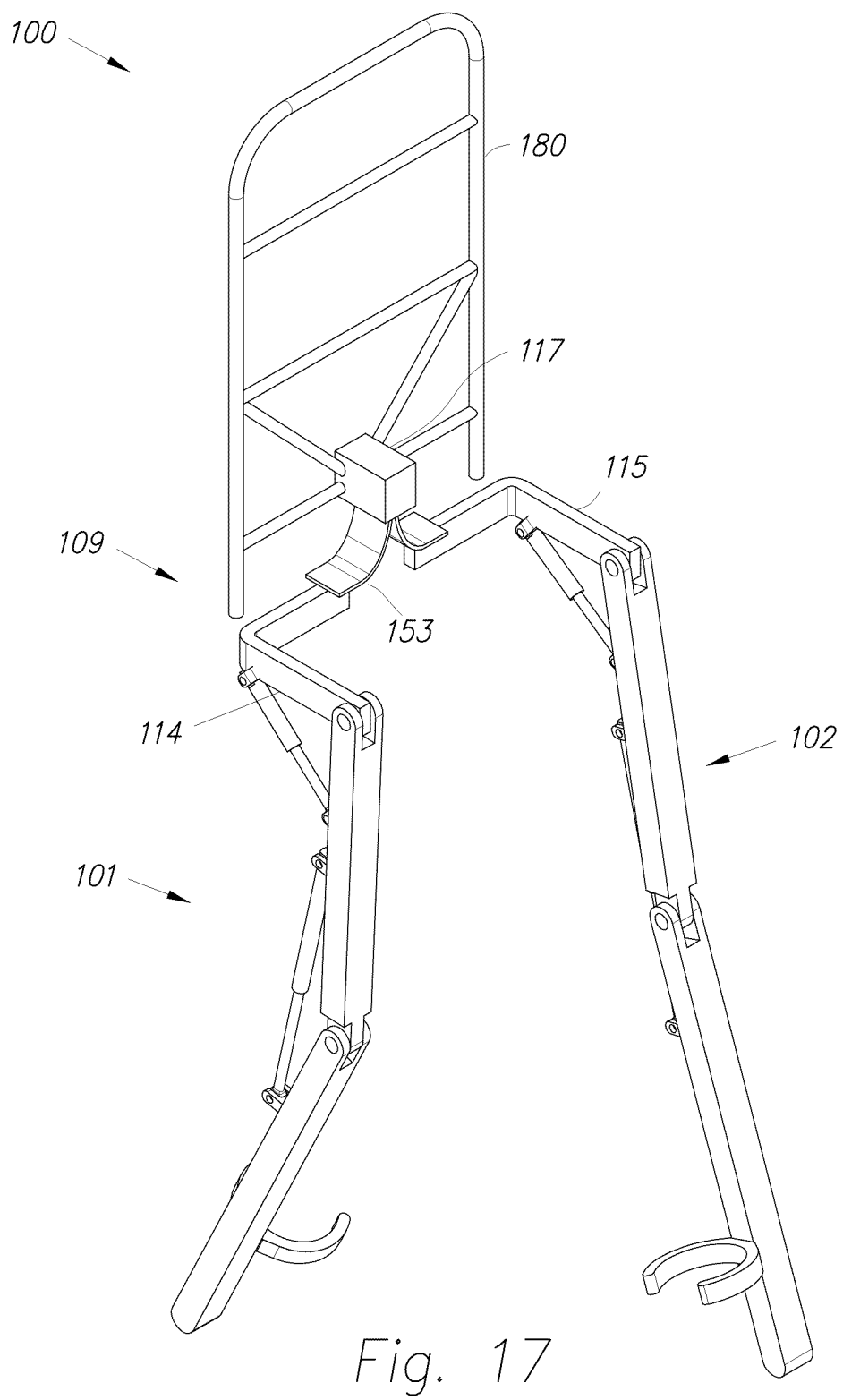
FIG. 17 is a perspective drawing of an alternative exoskeleton of the present invention including a back pack frame.

In some embodiments, as shown in FIG. 17, hip links 114 and 115 are compliantly connected to connecting bracket 117. In the embodiment shown in FIG. 17, this is accomplished by a hip resilient element 153, which in this case is a leaf spring.

In some embodiments, as shown in FIG. 17, exoskeleton trunk 109 comprises a backpack frame 180 that allows a backpack to be coupled to lower extremity exoskeleton 100. In some embodiments, backpack frame 180 is connected to connecting bracket 117. The upper body interface devices 150 (such as a belt and shoulder straps) have been omitted in this figure for clarity; however, upper body interface devices 150, in some embodiments, can be coupled to backpack frame 180 or connecting bracket 117.

Figure 18:
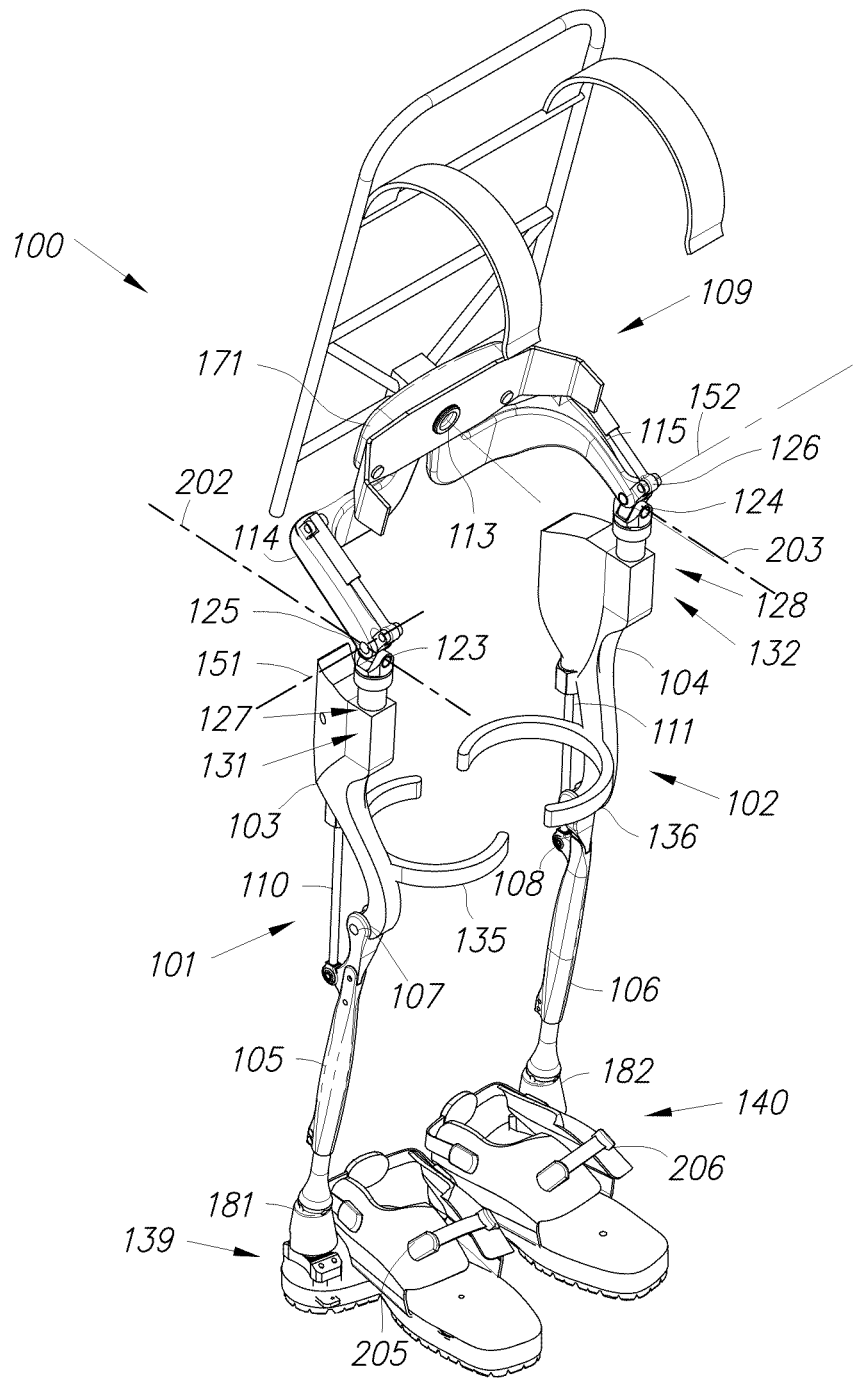
FIG. 18 is a perspective drawing of an alternative exoskeleton of the present invention including two hip resilient elements and exoskeleton feet.

In accordance with another embodiment, FIG. 18 is a perspective drawing wherein leg supports 101 and 102 further include thigh abduction-adduction joints 123 and 124, which are configured to allow abduction and/or adduction of leg supports 101 and 102 about thigh abduction-adduction axes 202 and 203, respectively. In some embodiments, thigh abduction-adduction joints 123 and 124 are located below hip flexion-extension joints 125 and 126. These joints are shown in greater detail in FIG. 19, which is a partial view of the same embodiment of FIG. 18.

Figure 19:
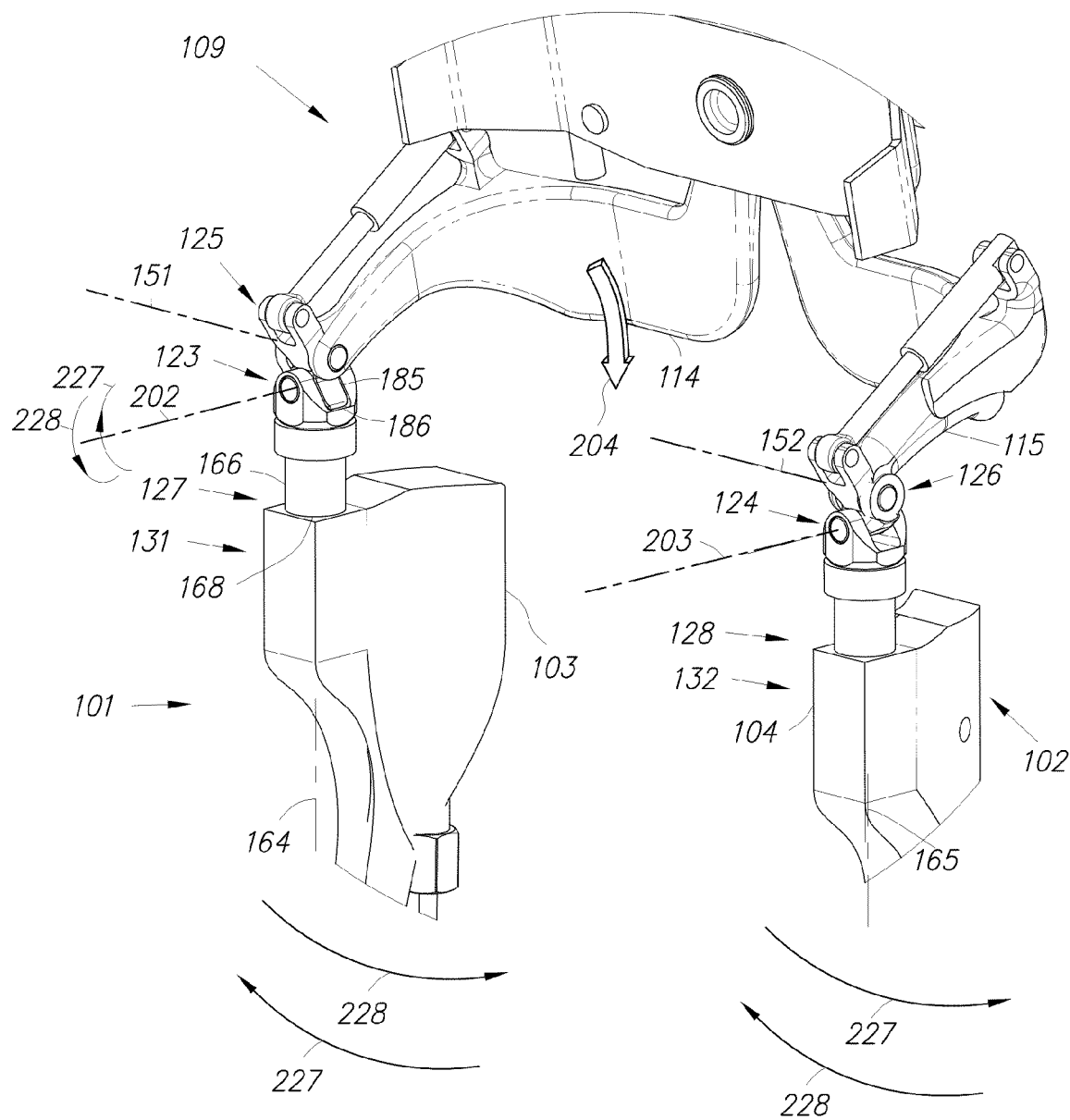
FIG. 19 is a partial view of the exoskeleton of FIG. 18, showing thigh joint details.

In some embodiments, as shown in FIG. 19, right leg support 101 includes a thigh adduction stop 185, which limits or prevents right thigh link 103 from adducting at thigh abduction-adduction joints 123 and 124. Abduction and adduction of right leg support 101 are shown by arrows 227 and 228, respectively. In the particular embodiment shown in FIG. 19, right thigh abduction-adduction joint 123 includes a thigh adduction stop 185, which bears on a thigh stop surface 186. Thigh adduction stop 185 limits the adduction of thigh abduction-adduction joint 123. The unrestricted adduction of right thigh abduction-adduction joint 123 during stance phase would cause right hip link 114 to move downwardly along arrow 204 during stance, thereby dropping (lowering) the load. Such abduction-only joints for thigh abduction-adduction joints 123 and 124 are useful in allowing the person to squat naturally. In some embodiments, like the ones shown in FIGS. 18 and 19, such abduction joints are generally located below hip flexion-extension joints 125 and 126.

Figure 20:
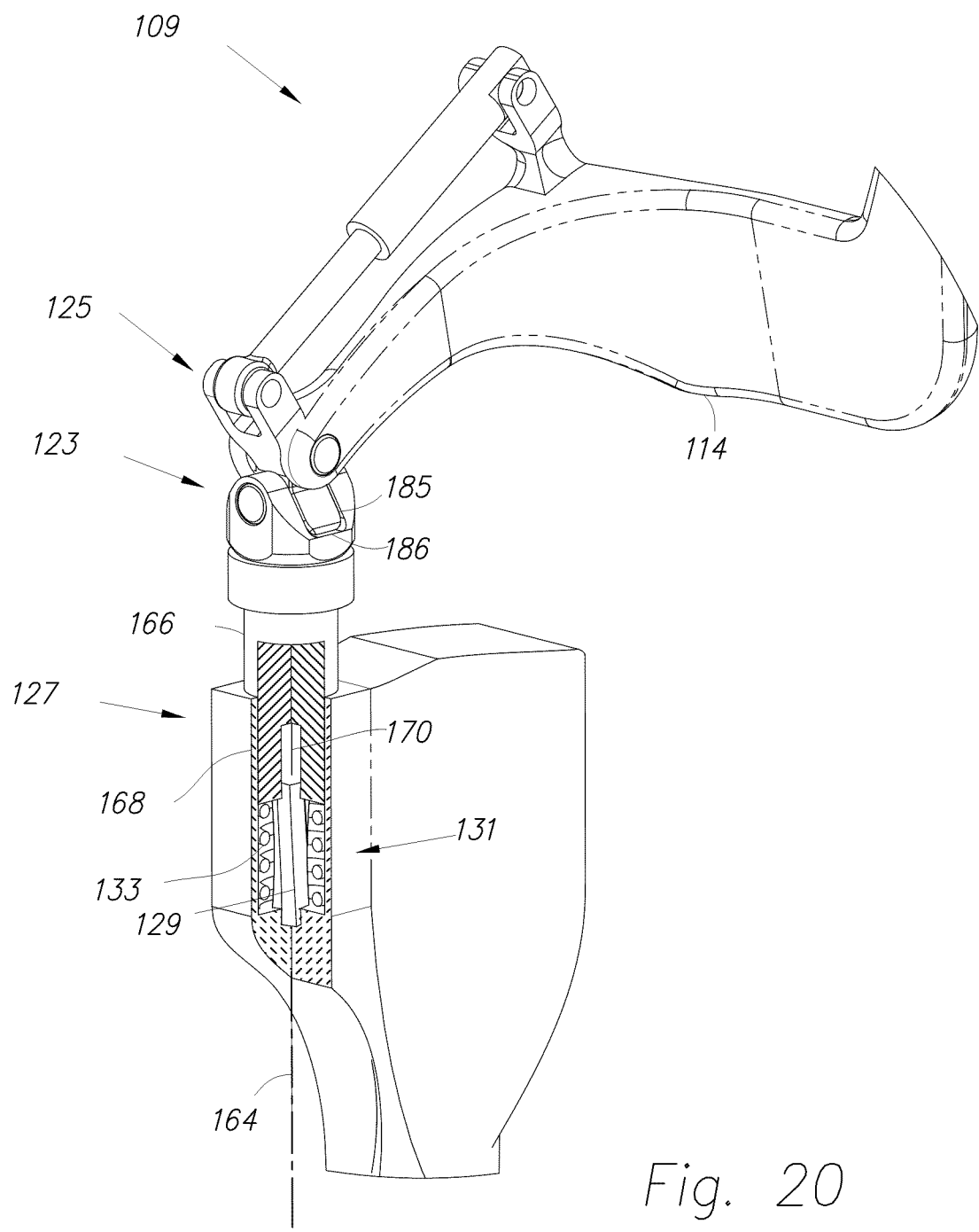
FIG. 20 is a partial view of the exoskeleton of FIG. 18 showing details of a compression-elongation mechanism.

In some embodiments, as shown in FIGS. 18 and 19, leg supports 101 and 102 further include leg rotation joints 127 and 128, configured to allow rotation of leg supports 101 and 102. Leg rotation joints 127 and 128 are generally located above knee joints 107 and 108. Lines 164 and 165 represent the leg rotation axes of leg rotation joints 127 and 128. In FIGS. 19 and 20, this is accomplished by providing for a sliding contact between the right hip rotation shaft 166 and the right hip rotation journal 168. The parts included in the joint, which prevent it from pulling apart, have been omitted for simplicity, but one skilled in the art will note that there are many ways of retaining such shafts in such journals.

In some embodiments, as shown in FIG. 20, leg rotation joints 127 and 128 further comprise a rotation resilient element 129. This rotation resilient element 129 acts as a torsion spring and provides a restoring torque that generally restores the leg support back to the neutral position shown in FIG. 18 from an extended position. Rotation resilient element 129 can be constructed in many ways, with the particular cross section shown in FIG. 20 being advantageous when using an elastomeric material to construct the element. Rotation resilient element 129 is shown, partially deflected for illustration purposes.

Also, in some embodiments, as shown in FIG. 19 and FIG. 20, leg supports 101 and 102 further comprise compression-elongation mechanisms 131 and 132 configured to change the distance between exoskeleton trunk 109 and the respective knee flexion-extension joints 107 and 108. In, some embodiments, compression-elongation mechanisms 131 and 132 allow for changes in the distance between the hip flexion-extension joints 125 and 126 and the respective flexion-extension knee joints 107 and 108. The compression-elongation mechanisms contracts by right hip rotation shaft 166 sliding further into the right hip rotation journal 168 (shown for right leg support 101 only). The leg rotation resilient element 129 is allowed to slide into a clearance cavity 170. In some embodiments, compression-elongation mechanisms 131 and 132 further comprise a right leg compression-elongation resilient element 133. This leg compression-elongation resilient element acts as a spring and provides a restoring force which generally restores the leg support back to a neutral configuration from an extended configuration. In the embodiment of FIG. 20, this is illustrated by a helical compression spring.

In some embodiments, as shown in FIG. 18, exoskeleton hip mechanism cover 171 may cover some components of the exoskeleton including parts of hip links 114 and 115, hip resilient element 153 or abduction-adduction hip resilient elements 121 and 122.

Figure 21:
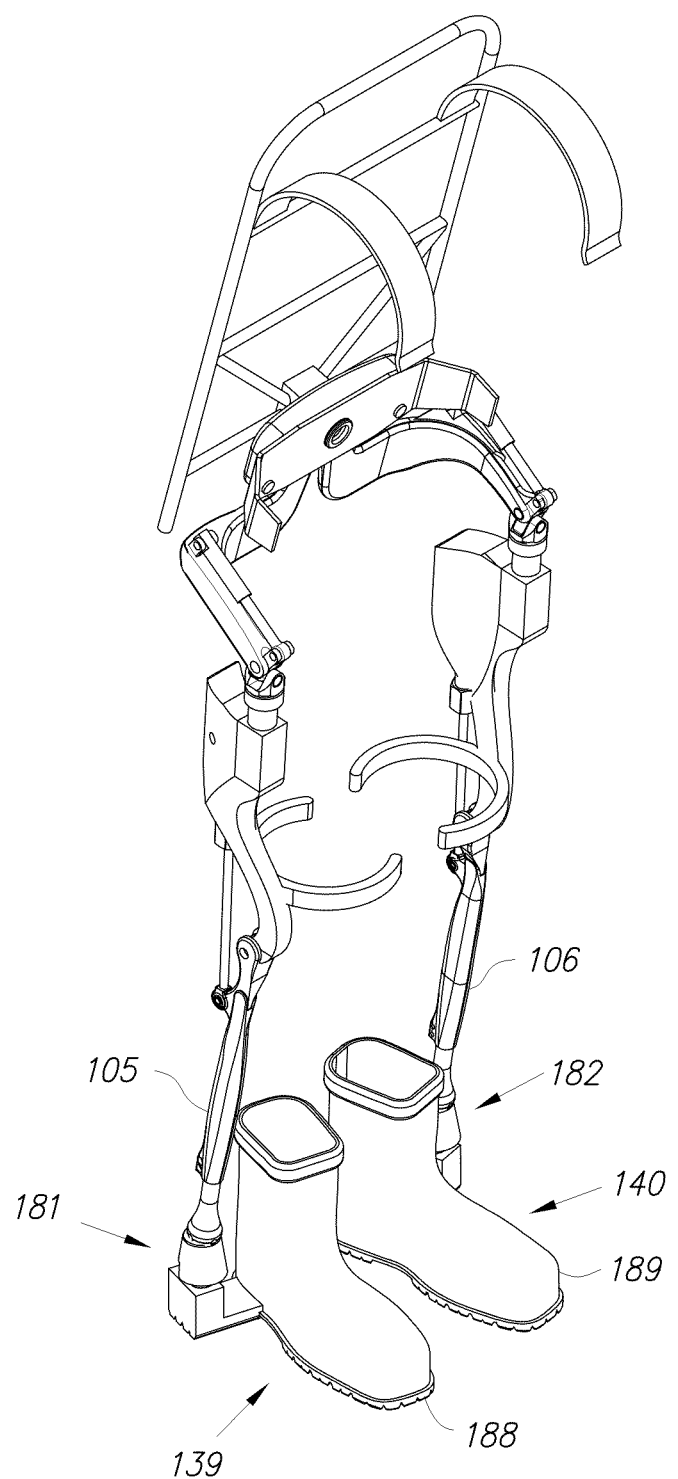
FIG. 21 is a perspective drawing of an alternative exoskeleton of the present invention including shoes.
Figure 22:
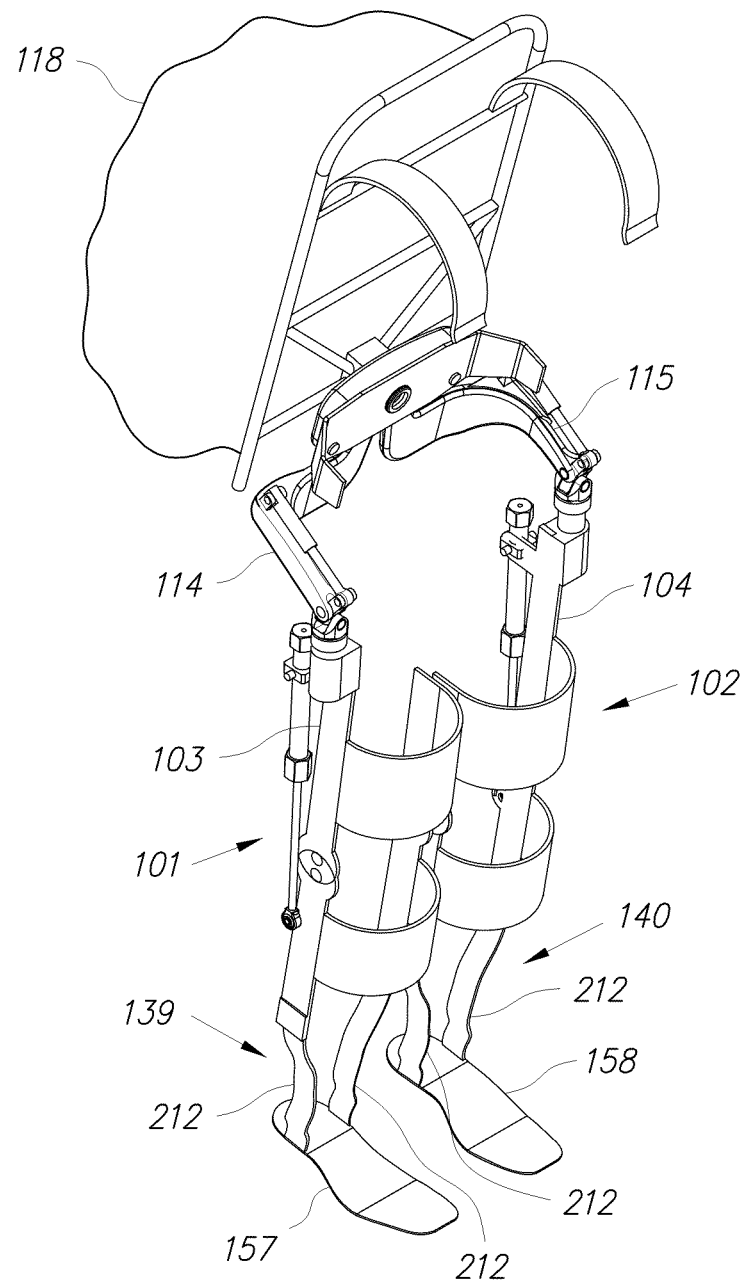
FIG. 22 is a perspective drawing of an alternative exoskeleton of the present invention including insoles.

In some embodiments, as shown in FIG. 18, leg supports 101 and 102 further comprise exoskeleton feet 139 and 140 coupled to shank links 105 and 106, respectively, allowing the transfer of forces from shank links 105 and 106 to the ground. In operation, exoskeleton feet 139 and 140 are configurable to be coupled to the feet of person 187. In some embodiments, as shown in FIG. 18, coupling to the person's feet is accomplished by using clam-shell type bindings 205 and 206, such as those sometimes found on modern snow shoes. However there are a great number of methods to make such a connection, as can be seen on different types of snow skis, snowboards, snowshoes and other such devices. In some embodiments, as shown in FIG. 21, exoskeleton feet 139 and 140 comprise exoskeleton shoes 188 and 189, wearable by person 187, thereby allowing exoskeleton feet 139 and 140 to couple to the feet of person 187. In some embodiments, as shown in FIG. 22, exoskeleton feet 139 and 140 comprise exoskeleton insoles 157 and 158, insertable inside the person's shoes, allowing exoskeleton feet 139 and 140 to couple to the feet of person 187. Insoles 157 and 158 are flexible and therefore can bend to match the curvature of the human foot during maneuvers such as squatting. Also, the insole side supports 212 are either compliant or configured to include degrees of freedom to mimic the movement of the human ankle.

Figure 23:
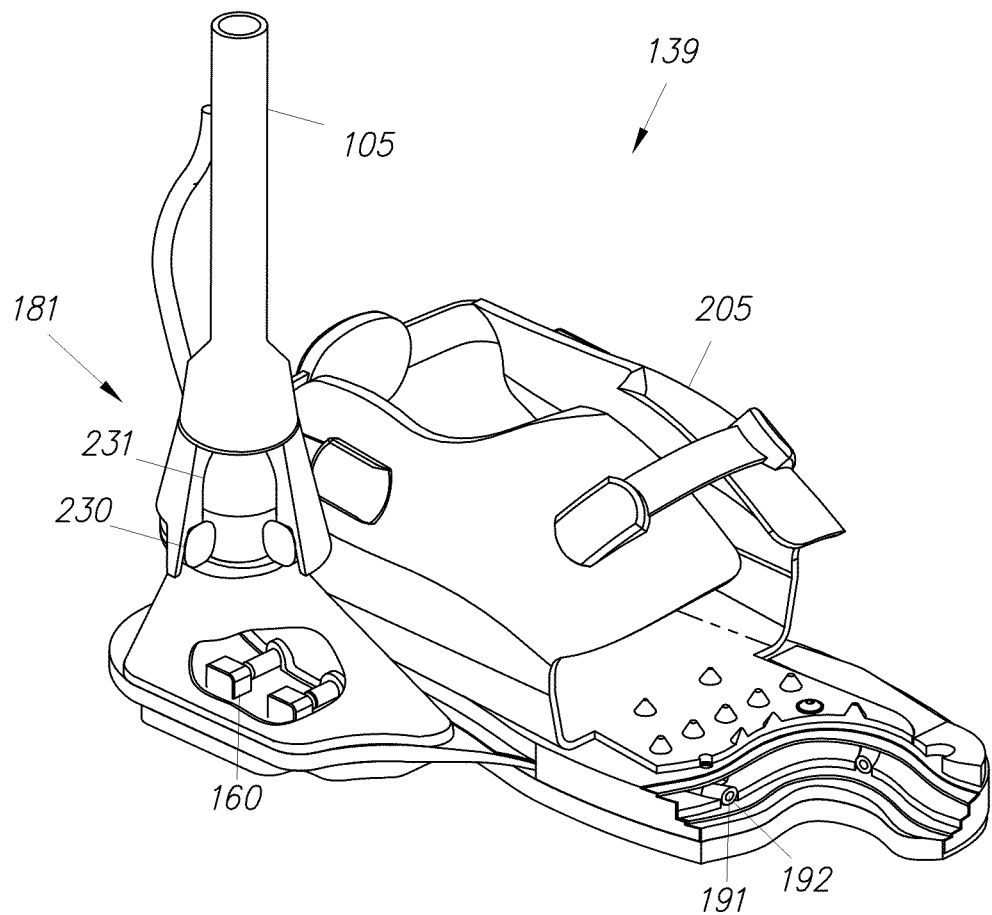
FIG. 23 is partial view of an exoskeleton foot of FIG. 18 including a ball and socket joint.

In some embodiments, as shown in FIG. 18, exoskeleton feet 139 and 140 are compliantly coupled to shank links 105 and 106. This is accomplished using ankle resilient elements 181 and 182. FIG. 23 shows a close-up view of right exoskeleton foot 139. In this example, right ankle resilient element 181 is constructed of a metal ball-and-socket joint 231 surrounded by a doughnut shaped elastomer element 230, which creates compliance in all directions of rotation.

Figure 24:
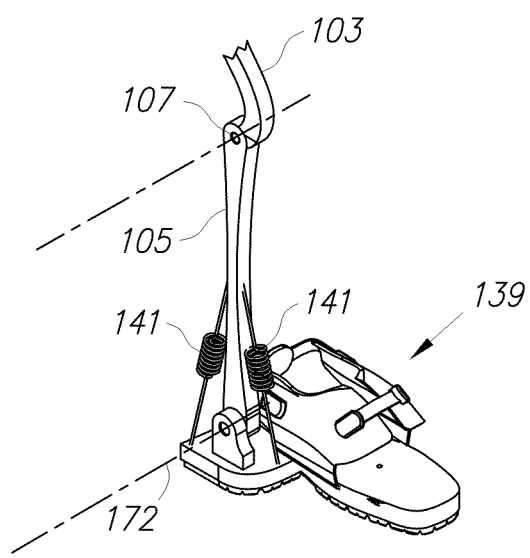
FIG. 24 is a perspective drawing of an alternative exoskeleton foot of the present invention including resilient elements.

In some embodiments, exoskeleton feet 139 and 140 rotate about two plantar-dorsi flexion axes relative to shank links 105 and 106. FIG. 24 shows an embodiment of this type of exoskeleton where right ankle plantar-dorsi flexion axis 172 is generally parallel to the plantar-dorsi flexion axis in, the human ankle. In some embodiments, each leg support further comprises at least one ankle plantar-dorsi flexion resilient element 141 resisting the rotation of respective exoskeleton foot about right ankle plantar-dorsi flexion axis 172.

Figure 25:
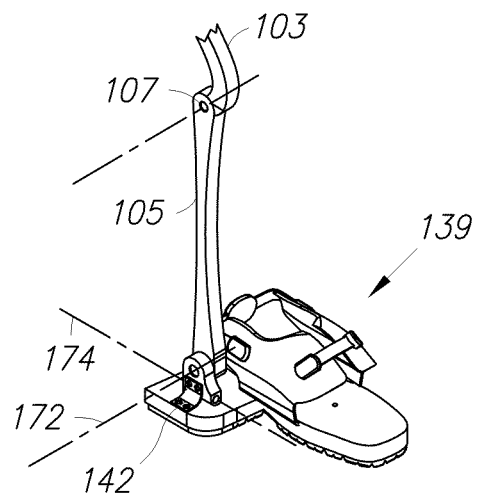
FIG. 25 is a perspective drawing of an alternative exoskeleton foot of the present invention including an abduction-adduction resilient element.

In some embodiments, exoskeleton feet 139 and 140 rotate about two ankle abduction-adduction axes relative to shank links 105 and 106. FIG. 25 shows an embodiment of this type of exoskeleton where right ankle abduction-adduction axis 174 is generally parallel to the abduction-adduction axis in the human ankle. In some embodiments, each leg support further comprises at least one ankle abduction-adduction resilient element 142 resisting the rotation of right exoskeleton foot 139 about right ankle abduction-adduction axis 174.

Figure 26:
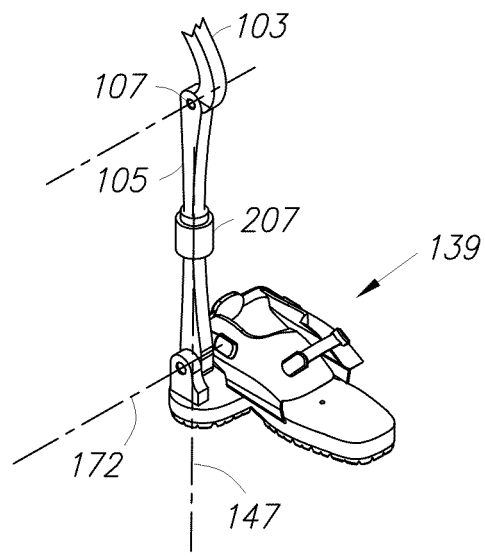
FIG. 26 is a perspective drawing of an alternative exoskeleton foot of the present invention including a shank rotating joint.

In some embodiments, exoskeleton feet 139 and 140 rotate about two ankle rotation axes 147 and 148 relative to shank links 105 and 106. In some embodiments, as shown in FIG. 26, this is accomplished using a shank rotation joint 207, which functions similar to leg rotation joint 127. FIG. 26 shows an embodiment of this type of exoskeleton where right ankle rotation axis 147 is generally parallel to the rotation axis in the human ankle. In some embodiments, resilient elements can be included in the ankle to resist the rotation of right exoskeleton foot 139 about right ankle rotation axis 147.

Figure 27:
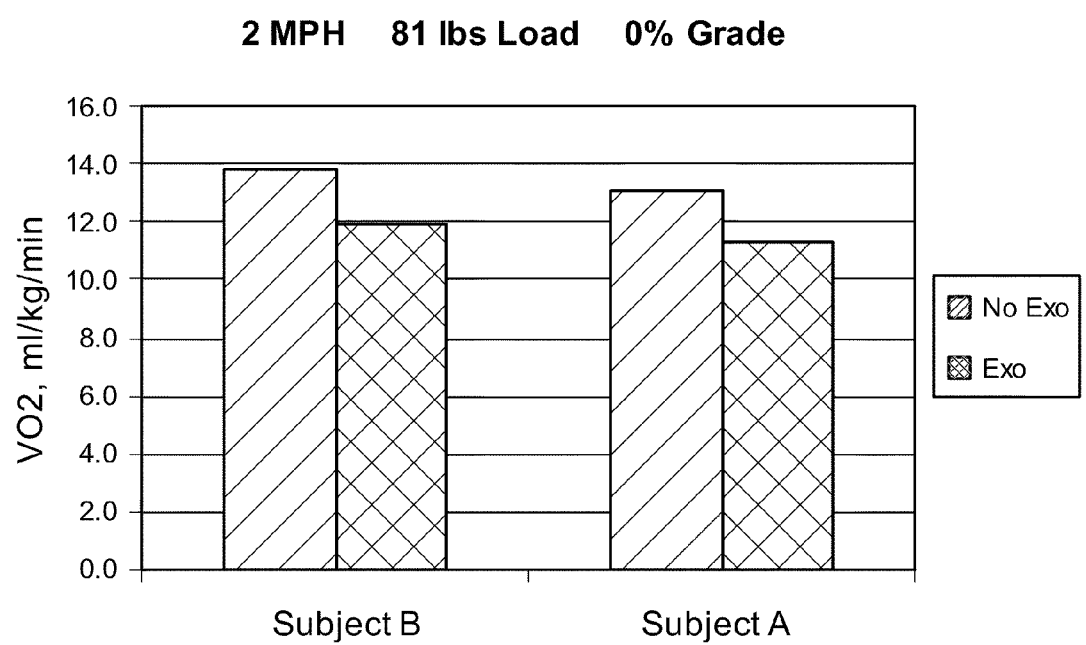
FIG. 27 is a chart showing oxygen consumption of subjects coupled to exoskeletons of the present invention compared to oxygen consumption of subjects with no exoskeleton.

Metabolic testing shows that oxygen consumption is reduced when using exoskeleton 100 to carry a load as compared to carrying a load without exoskeleton 100. Four tests are summarized in FIG. 27. In each test, a 14.3 kg vest was worn in the front (hung from exoskeleton 100 during exoskeleton tests) and 21.1 kg of load were attached to an external frame backpack (attached to exoskeleton 100 during exoskeleton tests), with the center of gravity of the backpack about 20 cm behind the subject's back. Additionally, the subjects wore a 1.4 kg helmet (not carried by exoskeleton 100). Each test was run for 10 minutes, and the last two minutes of data were averaged. Exoskeleton 100 created a torque profile as described above. Each subject's metabolic rate was decreased by about 14% when using exoskeleton 100 compared to, not using exoskeleton 100.

Figure 28:
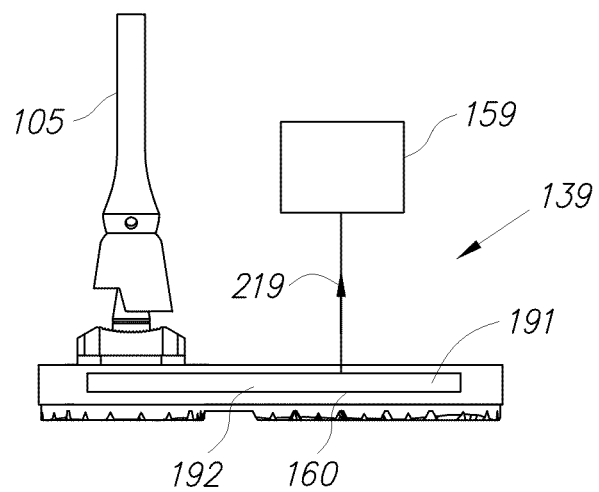
FIG. 28 is a partial cross-sectional side view of an alternative exoskeleton foot of the present invention including an integrated stance sensor.

In some embodiments, as shown in FIG. 28, stance sensors 160 and 161 are integrated into exoskeleton feet 139 and 140. In some embodiments, as shown in FIG. 28, stance sensor 160 is a pressure sensor, measuring the pressure in a media 191, trapped in a stance sensor cavity 192 inside right exoskeleton foot 139. FIG. 23 shows an embodiment where a tube is used as a stance sensor cavity 192. In some cases, the stance signals 219 and 220 may take the form of the media 191 transported in a small tube from stance sensor cavity 192 to signal processor 159.

Figure 29:
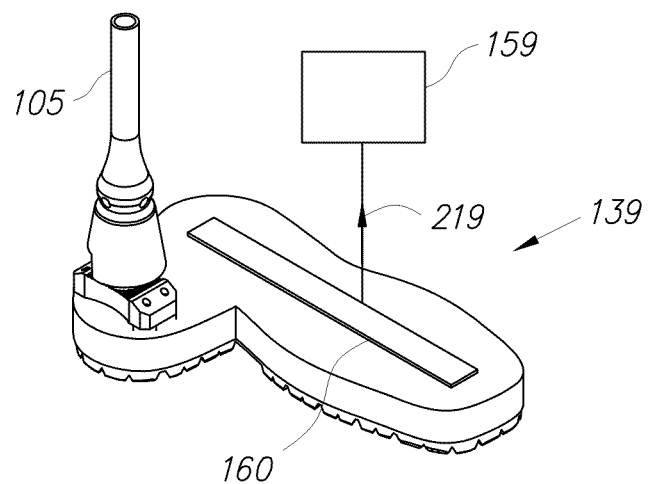
FIG. 29 is a top perspective view of an alternative exoskeleton foot of the present invention including a force sensor.
Figure 30:
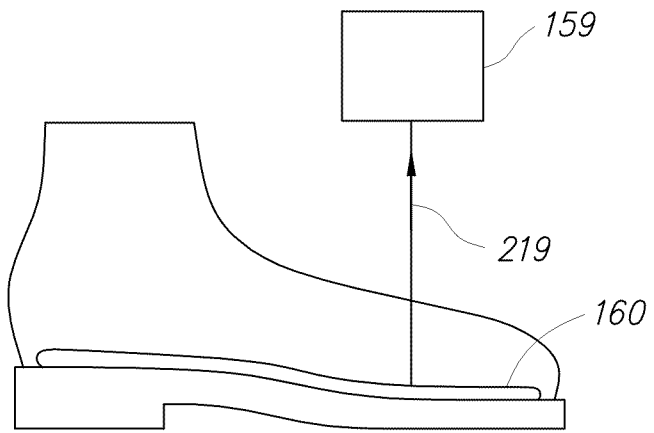
FIG. 30 is a partial cross-sectional side view of an alternative shoe of the present invention including an integrated stance sensor.
Figure 31:
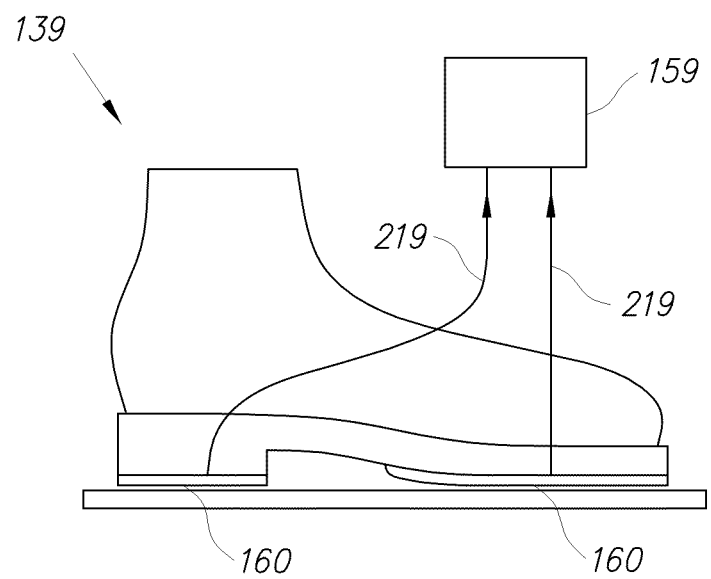
FIG. 31 is a partial cross-sectional side view of an alternative shoe of the present invention including a sole-mounted stance sensor.
Figure 32:
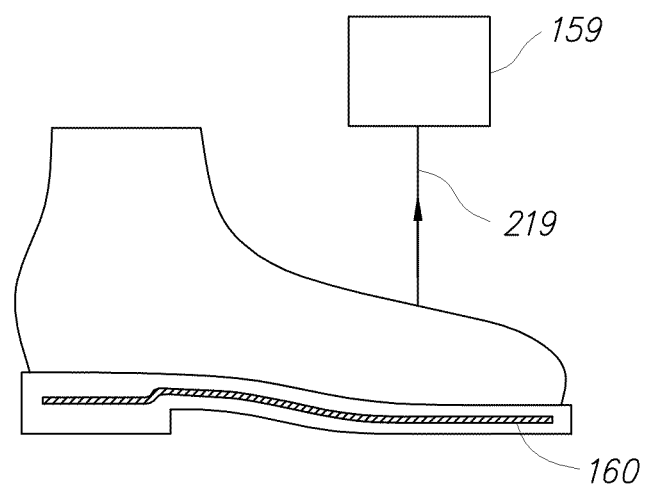
FIG. 32 is a partial cross-sectional side view of an alternative shoe of the present invention including a force sensor incorporated into the shoe sole.

FIG. 29 shows another embodiment wherein stance sensor 160 is a force sensor connectable to right exoskeleton foot 139. In some embodiments, as shown in FIG. 30, stance sensor 160 is located inside the human shoe like an insole, and its output signal represents the force on the bottom of the human foot. This type would be particularly useful in embodiments of the invention such as those shown in FIG. 21 or 22. In some embodiments, as shown in FIG. 31, stance sensor 160 is connected to the bottom of the human shoe and senses the force on the bottom of the human foot. In some embodiments, as shown in FIG. 32, stance sensor 160 is located inside the human shoe sole and senses the force on the bottom of the human foot. In some embodiments, stance sensors 160 and 161 are coupled to shank links 105 and 106, respectively.

Stance sensor 160 comprises any sensor or combination of sensors capable of performing the indicated functions. Examples of stance sensor 160 include, without limitation, force sensors, strain-gage based force sensors, piezoelectric force sensors, force sensing resistors, pressure sensors, switches, tape switches and combinations thereof. In some embodiments, stance sensor 160 is a switch that represents the existence of a force greater than some threshold force on the bottom of the foot of person 187.

Figure 33:
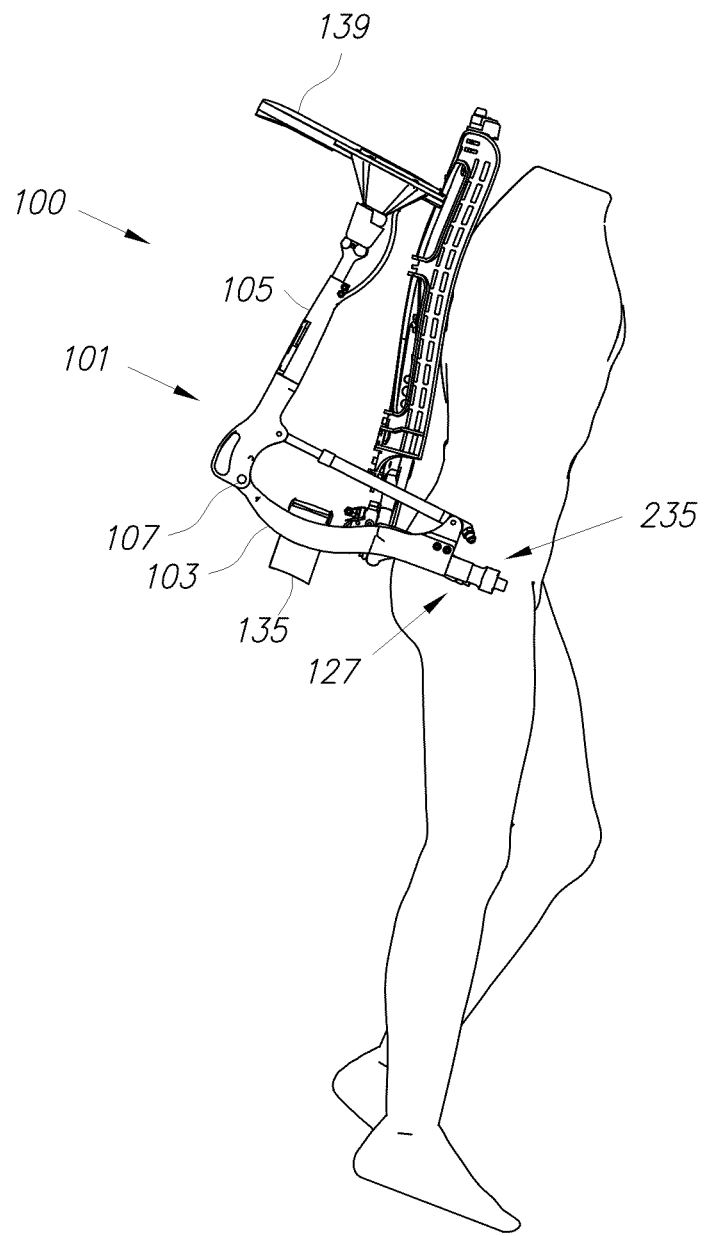
FIG. 33 is a side view of an alternative exoskeleton of the present invention carried in a vertical stowed position.
Figure 34:
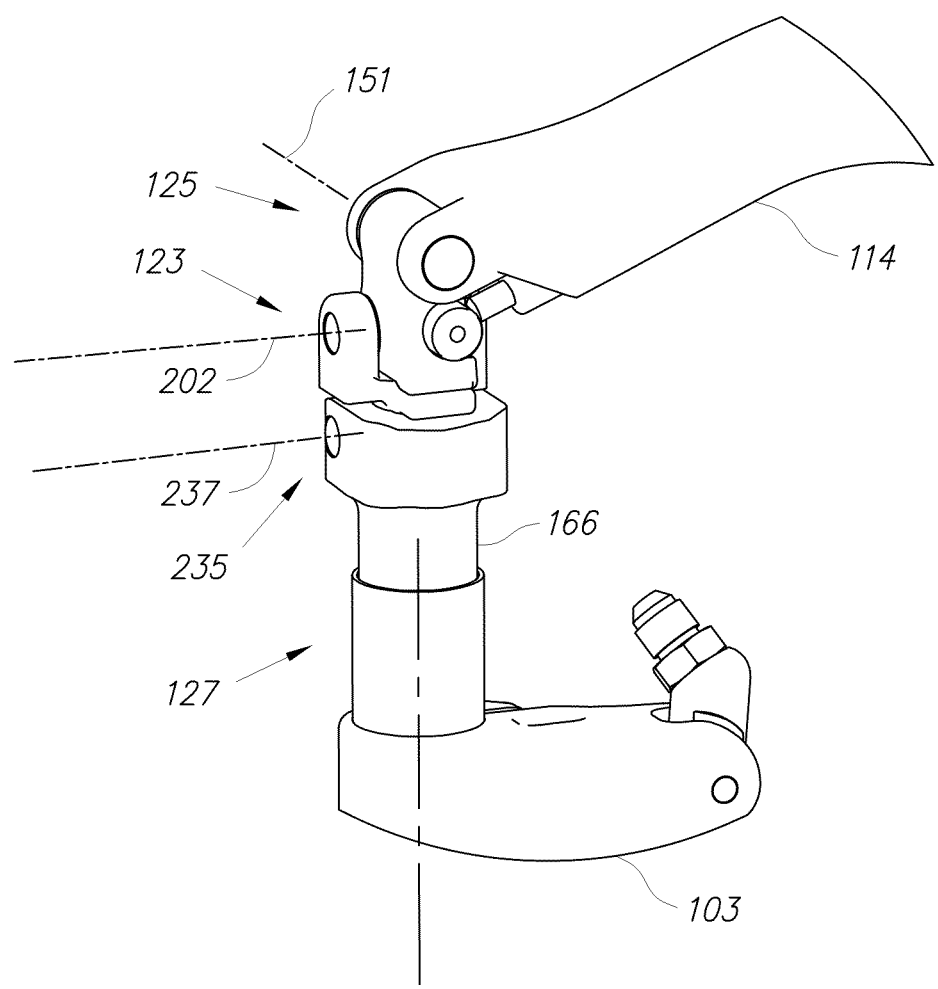
FIG. 34 is a partial perspective view of the exoskeleton of FIG. 33.

Also, shown in FIG. 33 is an additional thigh abduction-adduction joint 235, which is included in order to allow the leg to be stowed in a vertical position when the exoskeleton is not in use but needs to be carried. Right leg support 101 can abduct along an additional right thigh abduction-adduction axis 237 (shown in FIG. 34). This may be desirable if person 187 no longer has a very heavy load to carry but needs to transport lower extremity exoskeleton 100. In that case, the operator may unstrap the exoskeleton's right leg support 101 and swing the leg outward from his or her body until the right exoskeleton foot 139 is in the air over the operator's head. Then by bending the right knee joint 107 and/or rotating the right leg rotation joint 127, the leg can be positioned such that it stows behind the operator as shown in FIG. 33. This is possible because the right thigh abduction-adduction joint 123 and the additional right thigh abduction-adduction joint 235 each allow for a rotation of approximately ninety degrees about the right thigh abduction-adduction axis 202 and the additional right thigh abduction-adduction axis 237, respectively. The total abduction possible therefore is over 180 degrees. This could be accomplished with one thigh abduction-adduction joint which has 180 degrees of travel, but designing such a joint would cause the designer to move the pivot point of the joint outward from the operator a great deal, which would result in a wider exoskeleton design. This is undesirable but is a viable alternative design In some embodiments, lower extremity exoskeleton 100 (as shown in FIG. 1) comprises two torque generators 110 and 111, which are configured to allow flexion of knee joints 107 and 108 during swing phase and resist flexion of knee joints 107 and 108 during stance phase, thereby allowing the lower extremity exoskeleton 100 to bear a load and transfer the load forces (e.g., load weight) to the ground.

In some embodiments, torque generators 110 and 111 are hydraulic torque generators. In accordance with some embodiments, torque generators 110 and 111 are hydraulic piston cylinders where the motion of the piston relative to the cylinder creates hydraulic fluid flow into or out of the cylinder. In operation, the hydraulic fluid flow into or out of the cylinder may be controlled by a hydraulic valve. The smaller the hydraulic valve orifice size is, the more force is needed to move the piston relative to the cylinder with a given speed. In other words, the more damped the motion of the piston relative to the cylinder needs to be, the smaller the hydraulic valve orifice size should be. If the hydraulic valve orifice size is large, then a small force is required to move the piston relative to the cylinder. Here, impedance of hydraulic torque generators 110 and 111 is defined as the ratio of the required force over the velocity in frequency domain. With this definition, the smaller the hydraulic valve orifice size is, the larger the impedance of the hydraulic torque generator will be.

Figure 35:
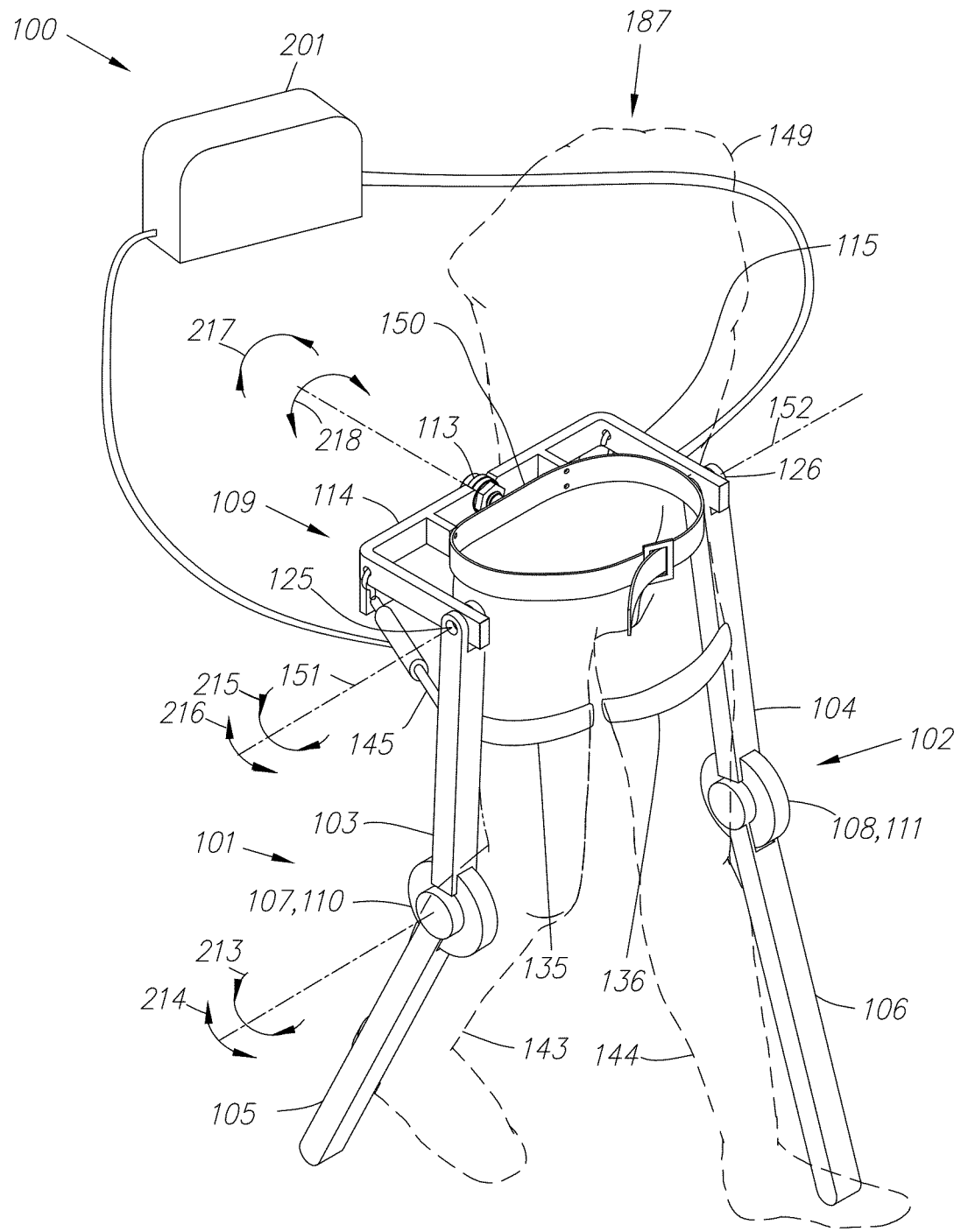
FIG. 35 is a perspective drawing of an alternative exoskeleton foot of the present invention including hydraulic rotary dampers.

In some embodiments, as shown in FIG. 35, torque generators 110 and 111 are hydraulic rotary dampers where the torque produced may be controlled by a hydraulic valve. The smaller the hydraulic valve orifice size is, the more torque is needed to rotate the hydraulic rotary damper with a given speed. In other words, the more damped the rotation of the hydraulic rotary damper needs to be, the smaller the hydraulic valve orifice size should be. Here, impedance of hydraulic rotary dampers 110 and 111 is defined as the ratio of the required torque over the angular velocity in frequency domain. With this definition, the smaller the hydraulic valve orifice size is, the larger the impedance of the hydraulic rotary damper will be.

In some embodiments, torque generators 110 and 111 are friction brakes where one can control the resistive torque on knee joints 107 and 108 by controlling the friction torques. In other embodiments, torque generators 110 and 111 are viscosity based friction brakes where one can control the resistive torque on knee joints 107 and 108 by controlling the viscosity of the fluid. In other embodiments, torque generators 110 and 111 are Magnetorheological Fluid Devices where one can control the resistive torque on knee joints 107 and 108 by controlling the viscosity of the Magnetorheological Fluid. One skilled in the art will realize that any of the above devices can be mounted in the invention to function in a manner corresponding to the hydraulic rotary dampers shown in FIG. 35.

In some embodiments, signal processor 159 is configured to control torque generators 110 and 111. Signal processor 159 controls the resistance to flexion in knee joints 107 and 108 as a function of stance signals 219 and 220. For example, when right stance sensor 160 detects the stance phase in right leg support 101, signal processor 159 will increase the impedance of right torque generator 110 so that right knee joint 107 resists flexion. Conversely, when right stance sensor 160 detects the swing phase in right leg support 101, signal processor 159 will decrease the impedance of right torque generator 110 so that no resistance to flexion occurs in right knee joint 107. Similarly, when stance sensor 160 detects the stance phase in left leg support 102, signal processor 159 will increase the impedance of left torque generator 111 so that left knee joint 108 resists flexion. Conversely, when left stance sensor 161 detects the swing phase in left leg support 102, signal processor 159 will decrease the impedance of left torque generator 111 so that no resistance to flexion occurs in left knee joint 108. Large impedances of torque generators 110 and 111 lead to a large resistance of knee joints 107 and 108 to flexion needed during stance phase. Conversely, small impedances of torque generators 110 and 1H lead to a small resistance of knee joints 107 and 108 to flexion needed during swing phase. In some embodiments, signal processor 159 is mounted to torque generators 110 and 111.

In practice, the resistance to flexion in knee joints 107 and 108 during the stance phase need not be constant. In some embodiments, the resistance to flexion at the beginning of the stance phase (approximately the first 20% of the stance cycle) may be extremely high (i.e., knee joints 107 and 108 will be locked in the beginning of stance). During the middle of the stance phase (approximately the 20% to 80% of the stance cycle), the resistance to flexion may be lower, but high enough that knee joints 107 and 108 will only undergo a few degrees of Flexion. During the end of the stance cycle (approximately the last 20% of the stance cycle), the resistance to flexion may be low, but still nonzero, so that knee joints 107 and 108 may flex in preparation for the swing cycle.

Figure 36:
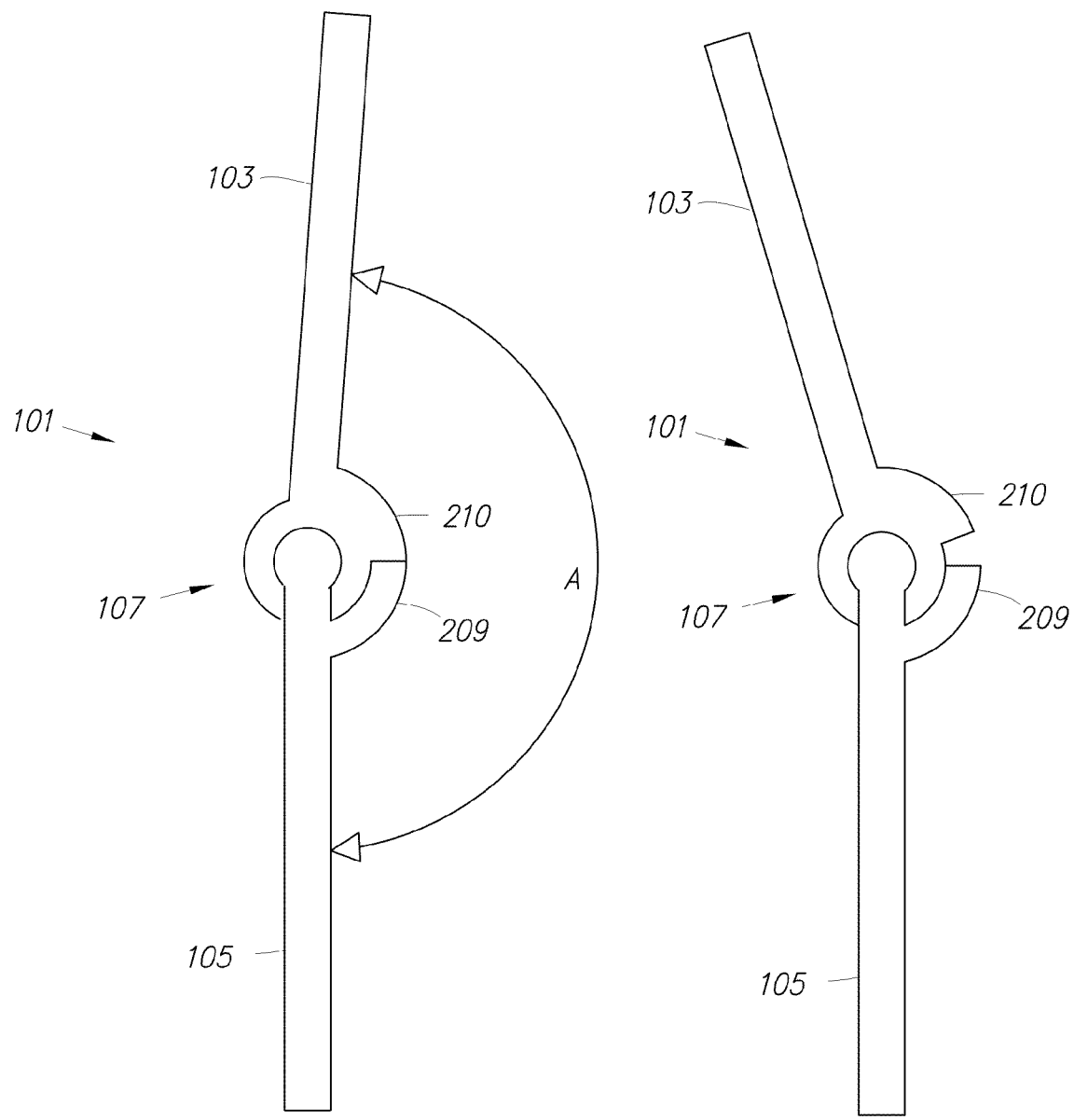
FIG. 36 depicts the function of a locking knee joint in accordance with the present invention.

In some embodiments, leg supports 101 and 102 are configured to allow flexion of the respective knee joints 107 and 108 during the swing phase, and to resist flexion of the respective knee joints 107 and 108 during the stance phase, by locking the knees. One such locking, knee is shown in FIG. 36. Actually, FIG. 36 shows right leg support 101 in two configurations. More specifically, right shank link 105 includes a shank stop 209, which bears on, thigh stop 210 when the knee is hyperextended. The angle of right knee joint 107 at hyper-extension is illustrated as A in FIG. 36. Since this angle is less than 180 degrees, knee joint 107 or 108 will go "over-center" when approaching hyper-extension, meaning that the knee will tend to lock against the stops if leg supports 101 or 102 is subject to a compressive load, as would be the case for right leg support 101 in the situation illustrated in FIG. 36. With this recognition, one skilled in the art will note that various over-center mechanisms could, be employed to force the load vector onto the leg support to pass in front of the knee joint.

Figure 37:
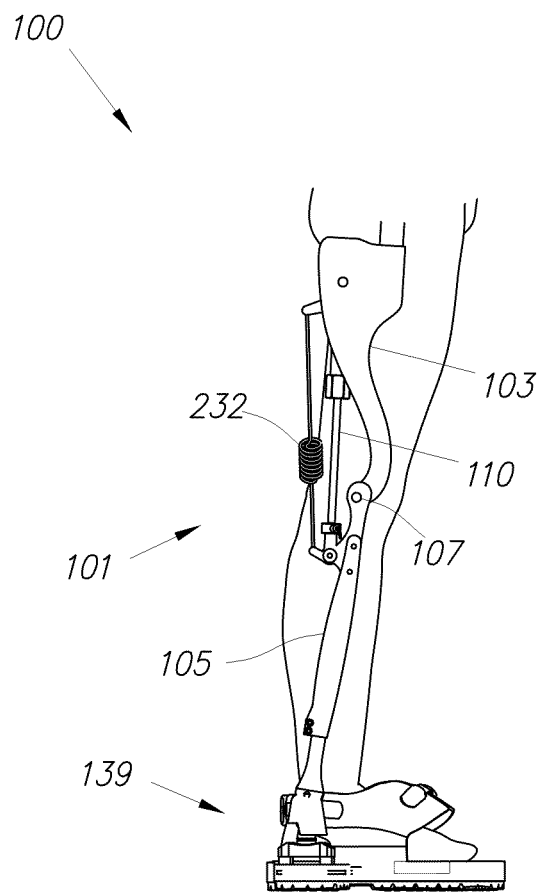
FIG. 37 is a side view of an alternative right leg support of the present invention including knee resilient elements in parallel with torque generators.
Figure 38:
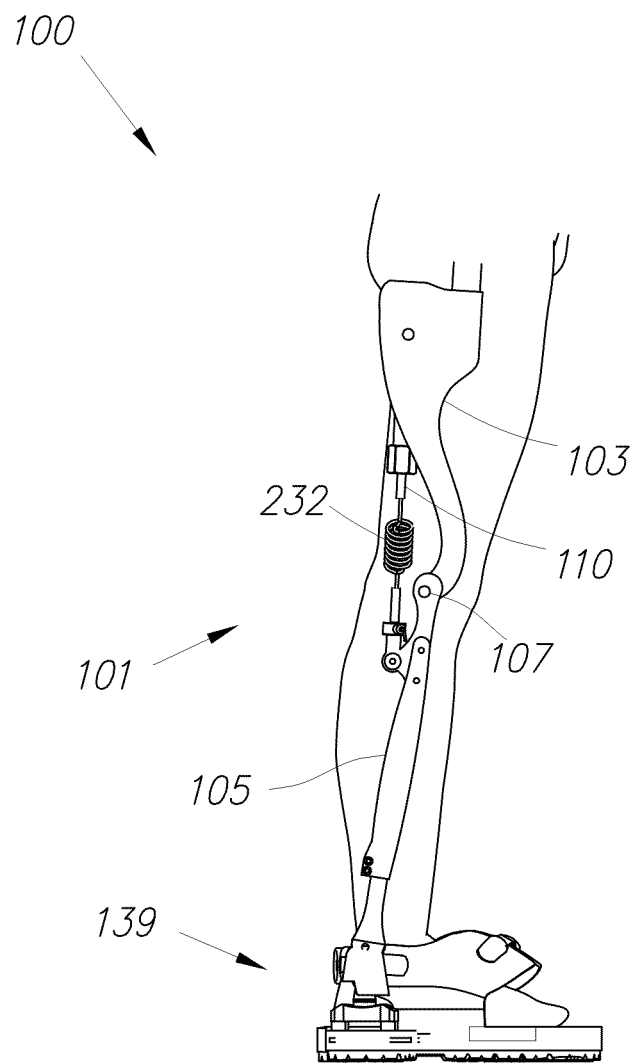
FIG. 38 is a side view of an alternative right leg support of the present invention including knee resilient elements in series with torque generators.

In some embodiments, lower extremity exoskeleton 100 further comprises knee resilient elements 232, which are configured to encourage flexion of knee joints 107 and 108. This decreases the person's effort needed to flex knee joints 107 and 108 during the swing phase. In some embodiments, as shown in FIG. 37, knee resilient elements 232 are in parallel with torque generators 110 and 111. In some embodiments, knee resilient elements 232, as shown in FIG. 38, are in series with torque generators 110 and 111. In some embodiments, lower extremity exoskeleton 100 comprises knee resilient elements 232, which are configured to encourage extension of knee joints 107 and 108. In general, in accordance with the invention, there are many methods and locations for, installation of knee resilient element 232 to encourage flexion and/or extension of knee joints 107 and 108. It is further understood that knee resilient elements 232 can also be used with, the embodiment of the exoskeleton shown in FIG. 36.

According to experiments conducted, the exoskeleton of the invention significantly decreases the wearer's oxygen consumption. During evaluation, the oxygen consumption of a user walking without a payload at a speed of 2 MPH was decreased by 5%~12% when using the exoskeleton of the present invention. When the user carried a load, the effect was more pronounced. For instance, the oxygen consumption of the user carrying an 81 pound load at a speed of 2 MPH was decreased by about 15% when using this exoskeleton to carry the same load. Therefore, the load-carrying exoskeleton of the invention provides for a significant decrease in oxygen consumption of the user. In any case, although various exemplary embodiments have been described, it will be appreciated by persons skilled in the art that numerous variations and/or modifications may be made to the described device as specifically shown here without departing from the spirit or scope of that broader disclosure. Therefore, the various examples are to be considered in all respects as illustrative and not restrictive. In general, the invention is only intended to be limited by the scope of the following claims.

We claim:

1. A method of reducing the oxygen consumption of a person during a walking cycle utilizing an exoskeleton device, adapted to be coupled to said person, including at least one power unit, first and second leg supports rotatably connected to an exoskeleton trunk, and first and second hip actuators configured to create torques between said exoskeleton trunk and said first and second leg supports respectively, said method comprising:

creating a first unidirectional torque utilizing said first hip actuator, when said first leg support enters a stance phase, to move said first leg support in the stance phase backward relative to said exoskeleton trunk thereby pushing the exoskeleton trunk in a forward direction until said second leg support in a swing phase enters a stance phase such that the exoskeleton device is in the double stance condition; and creating a second unidirectional torque utilizing said first hip actuator, when said second leg support enters the stance phase, to move said first leg support while still in the stance phase forward until said first leg support leaves a support surface and moves into a swing phase.

2. The method of claim 1 wherein a magnitude of said second unidirectional torque is generally smaller than a magnitude of said first unidirectional torque.

3. The method of claim 1 wherein said first unidirectional torque is generally constant.

4. The method of claim 1 wherein said second unidirectional torque is generally constant.

5. The method of claim 1 wherein moving said first leg support into the swing phase comprises creating a swing torque, utilizing the first hip actuator, acting in a direction to move said first leg support forwardly relative to said exoskeleton trunk.

6. The method of claim 5 wherein said swing torque is equal to said second unidirectional torque.

7. The method of claim 1 wherein said first unidirectional torque is decreasing in value when first leg support is in the stance phase and said second leg support is in the swing phase.

8. The method of claim 1 wherein a sum of the torques from said hip actuators onto said exoskeleton trunk acts in a direction of hip extension at all times.

9. The method of claim 8 wherein the sum of the torques from said hip actuators onto said exoskeleton trunk is generally constant.

10. The method of claim 8 wherein the sum of the torques from said hip actuators onto said exoskeleton trunk drops to no less than 50% of its maximum value at any time.

11. The method of claim 5 wherein said swing torque is unidirectional during the swing phase of the first leg support.

12. The method of claim 5 wherein a magnitude of said swing torque generally decreases over a period of swing.

13. The method of claim 5 wherein said swing torque starts at a value equal to said second unidirectional torque and then generally decreases over a period of swing.

14. The method of claim 5 wherein said swing torque is near zero in late swing.

15. The method of claim 5 wherein said swing torque has a magnitude which decreases over a period of swing until said swing torque switches direction in late swing.

16. The method of claim 5 wherein said swing torque includes a torque proportional to an angular velocity of said first leg support in swing with respect to said exoskeleton trunk, and acts in a direction that increases said angular velocity.

17. The method of claim 5 wherein said swing torque includes a torque proportional to an angular velocity of said first leg support in swing with respect to the support surface, and acts in a direction that increases said angular velocity.

18. The method of claim 5 wherein said swing torque includes a torque proportional to an angular acceleration of said first leg support with respect to said exoskeleton trunk, and acts in a direction that increases said angular acceleration.

19. The method of claim 5 wherein said swing torque includes a torque proportional to an angular acceleration of said first leg support with respect to a support surface, and acts in a direction that increases said angular acceleration.

20. The method of claim 5 wherein said swing torque includes a torque proportional to a sine of a hip angle of said first leg support with respect to said exoskeleton trunk, and acts in a direction to oppose gravity of said first leg support.

21. The method of claim 5 wherein said swing torque includes a torque which is proportional to a sine of a hip angle of said first leg support with respect to the support surface and acts in a direction to oppose gravity of said first leg support.

22. The method of claim 5 wherein said first unidirectional torque is a summation including a component which is proportional to a negative value of a swing torque generated by said second hip actuator of said second leg support in the swing phase.

23. A method of reducing the oxygen consumption and heart rate of a person during a walking cycle utilizing an exoskeleton device, adapted to be coupled to said person, including at least one power unit, first and second leg supports rotatably connected to an exoskeleton trunk and configured to rest on a support surface during their stance phases, and first and second hip actuators configured to create torques between said exoskeleton trunk and said first and second leg supports respectively, said method comprising:

creating a first unidirectional torque utilizing said first hip actuator, when said first leg support strikes the support surface and enters a stance phase, to move said first leg support in the stance phase backward relative to said exoskeleton trunk thereby pushing said person's upper body in a forward direction until said second leg support in a swing phase strikes the support surface such that the exoskeleton device is in the double stance condition; and creating a second unidirectional torque utilizing said first hip actuator, when said second leg support strikes the support surface and enters a stance phase, to move said first leg support, while still in the stance phase, forward until said first leg support leaves the support surface and then moving said first leg support into a swing phase.

* * * * *